(12) United States Patent
Santra et al.

(10) Patent No.: US 7,618,434 B2
(45) Date of Patent: Nov. 17, 2009

(54) DEVICES AND METHODS FOR DISRUPTION AND REMOVAL OF LUMINAL OCCLUSIONS

(75) Inventors: Swadeshmukul Santra, Gainesville, FL (US); Robert A. Mericle, Gainesville, FL (US); Christopher D. Batich, Gainesville, FL (US); Jessie T. Stanley, Trenton, FL (US); Eric Eskioglu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/844,737

(22) Filed: May 12, 2004

(65) Prior Publication Data

US 2005/0033334 A1    Feb. 10, 2005

Related U.S. Application Data

(60) Provisional application No. 60/470,067, filed on May 12, 2003.

(51) Int. Cl.
*A61M 29/00* (2006.01)
(52) U.S. Cl. ..................................... 606/200
(58) Field of Classification Search .............. 606/113, 606/114, 127, 159, 191–200; 604/22, 104–107
See application file for complete search history.

(56) References Cited

U.S. PATENT DOCUMENTS

| 3,435,826 A | 4/1969 | Fogarty |
| 3,467,101 A | 9/1969 | Fogarty et al. |
| 4,403,612 A | 9/1983 | Fogarty |
| 4,611,594 A | 9/1986 | Grayhack et al. |

(Continued)

FOREIGN PATENT DOCUMENTS

EP    0 331 040 B1    9/1989

(Continued)

OTHER PUBLICATIONS

Antani, M.R. "Catheter-directed thrombolysis for the treatment of acute deep venous thrombosis" *Supp. Applied Radiol.*, 2001, 29-35.

(Continued)

*Primary Examiner*—Todd E Manahan
*Assistant Examiner*—Lindsey Bachman
(74) *Attorney, Agent, or Firm*—Saliwanchik, Lloyd & Saliwanchik

(57) ABSTRACT

The subject invention pertains to an elastic sheath, device, and methods for disrupting and/or removing occlusive material from lumens, particularly biological lumens, such as the vasculature, ureter, urethra, fallopian tubes, bile duct, intestines, and the like. The subject invention provides for effective disruption and removal of occlusive material, such as a thrombus, from the body lumen with minimal risk of injury to the lumen wall. Advantageously, the invention can be used to achieve a high degree of removal while minimizing the amount of occlusive material that is released into the body lumen. The subject invention further pertains to methods for disrupting and removing occlusive material from a biological lumen. In another aspect, the present invention concerns a device useful as an in vitro model of luminal occlusion and methods for using the device to test the efficacy of devices and methods for treating luminal occlusions.

28 Claims, 7 Drawing Sheets
(2 of 7 Drawing Sheet(s) Filed in Color)

U.S. PATENT DOCUMENTS

| | | |
|---|---|---|
| 4,621,636 A | 11/1986 | Fogarty |
| 4,637,396 A | 1/1987 | Cook |
| 4,646,736 A | 3/1987 | Auth |
| 4,762,130 A | 8/1988 | Fogarty et al. |
| 4,919,651 A | 4/1990 | Doane |
| 4,928,858 A | 5/1990 | Tite |
| 5,084,065 A | 1/1992 | Weldon et al. |
| 5,116,352 A | 5/1992 | Schnepp-Pesch et al. |
| 5,226,909 A | 7/1993 | Evans et al. |
| 5,232,445 A | 8/1993 | Bonzel |
| 5,250,029 A | 10/1993 | Lin et al. |
| 5,320,634 A | 6/1994 | Vigil et al. |
| 5,330,484 A | 7/1994 | Gunther et al. |
| 5,334,211 A | 8/1994 | Shiber |
| 5,370,682 A | 12/1994 | Schmitt |
| 5,410,093 A | 4/1995 | Dorai |
| 5,419,774 A | 5/1995 | Willard et al. |
| 5,423,799 A | 6/1995 | Shiu |
| 5,501,408 A | 3/1996 | Kang et al. |
| 5,540,707 A * | 7/1996 | Ressemann et al. ......... 606/159 |
| 5,556,408 A | 9/1996 | Farhat |
| 5,569,275 A | 10/1996 | Kotula et al. |
| 5,569,277 A | 10/1996 | Evans et al. |
| 5,681,335 A | 10/1997 | Serra et al. |
| 5,695,501 A | 12/1997 | Carol et al. |
| 5,695,507 A | 12/1997 | Auth et al. |
| 5,766,191 A | 6/1998 | Trerotola |
| 5,795,322 A | 8/1998 | Boudewijn |
| 5,824,037 A | 10/1998 | Fogarty et al. |
| 5,824,049 A | 10/1998 | Ragheb et al. |
| 5,868,708 A * | 2/1999 | Hart et al. ................... 604/104 |
| 5,904,698 A * | 5/1999 | Thomas et al. .............. 606/159 |
| 5,911,734 A | 6/1999 | Tsugita et al. |
| 5,928,186 A | 7/1999 | Homsma et al. |
| 5,947,985 A | 9/1999 | Imran |
| 5,954,737 A | 9/1999 | Lee |
| 5,954,745 A * | 9/1999 | Gertler et al. ............... 606/200 |
| 5,972,019 A * | 10/1999 | Engelson et al. ............ 606/200 |
| 6,120,477 A | 9/2000 | Campbell et al. |
| 6,152,946 A | 11/2000 | Broome et al. |
| 6,156,064 A | 12/2000 | Chouinard |
| 6,165,212 A | 12/2000 | Dereume et al. |
| 6,277,139 B1 | 8/2001 | Levinson et al. |
| 6,319,242 B1 * | 11/2001 | Patterson et al. ............ 604/508 |
| 6,361,545 B1 | 3/2002 | Macoviak et al. |
| 6,454,775 B1 | 9/2002 | Demarais et al. |
| 6,485,512 B1 | 11/2002 | Cheng |
| 6,530,940 B2 | 3/2003 | Fisher |
| 6,547,804 B2 | 4/2003 | Porter et al. |
| 6,558,405 B1 * | 5/2003 | McInnes ..................... 606/200 |
| 6,629,953 B1 * | 10/2003 | Boyd ......................... 604/106 |
| 6,635,070 B2 * | 10/2003 | Leeflang et al. ............. 606/200 |
| 7,048,752 B2 * | 5/2006 | Mazzocchi et al. .......... 606/200 |
| 2001/0031981 A1 | 10/2001 | Evans et al. |
| 2002/0010489 A1 | 1/2002 | Grayzel et al. |
| 2002/0082638 A1 | 6/2002 | Porter et al. |
| 2002/0099431 A1 | 7/2002 | Armstrong et al. |
| 2002/0161342 A1 | 10/2002 | Rivelli, Jr. et al. |
| 2002/0169497 A1 | 11/2002 | Wholey et al. |
| 2002/0173819 A1 | 11/2002 | Leeflang et al. |
| 2002/0183782 A1 * | 12/2002 | Tsugita et al. .............. 606/200 |

FOREIGN PATENT DOCUMENTS

| | | |
|---|---|---|
| EP | 0 348 573 A1 | 1/1990 |
| EP | 0 416 662 A2 | 3/1991 |
| EP | 0 418 677 A1 | 3/1991 |
| EP | 0 419 154 A1 | 3/1991 |
| EP | 0 479 433 A2 | 4/1992 |
| EP | 0 549 458 B1 | 6/1993 |
| EP | 0 565 395 B1 | 10/1993 |
| EP | 0 596 928 B1 | 5/1994 |
| EP | 0 619 720 B1 | 10/1994 |
| EP | 0 737 450 A1 | 10/1996 |
| EP | 0 744 189 A1 | 11/1996 |
| EP | 0 820 729 A1 | 1/1998 |
| EP | 0 832 608 A2 | 4/1998 |
| EP | 0 834 287 A1 | 4/1998 |
| EP | 1 199 082 A1 | 4/2002 |
| WO | WO 96/01591 A1 | 1/1996 |
| WO | WO 99/44510 A1 | 9/1999 |
| WO | WO 99/44542 A2 | 9/1999 |

OTHER PUBLICATIONS

Kasirajan K. et al. "The use of mechanical thrombectomy devices in the management of acute peripheral arterial occlusive disease" *J. Vasc. Interv. Radiol.*, 2001, 12:405-411.

Nutting, C. and Coldwell, D. "Use of a TrapEase device as a temporary caval filter" *J. Vasc Interv. Radiol.*, 2001, 12:991-993.

Schmitz-Rode, T. and Gunther, R. "New device for percutaneous fragmentation of pulmonary emboli" *Radiology*, 1991, 180:135-137.

Sharafuddin, M. and Hicks, M. "Current status of percutaneous mechanical thrombectomy. Part I. General principles" *J. Vasc. Interv. Radiol.*, 1997, 8:911-921.

Vorwerk, D. et al. "Percutaneous balloon embolectomy with a self-expanding tulip sheath: In vivo experiments" *Radiology*, 1995, 197:153-156.

* cited by examiner

DEVICES AND METHODS FOR DISRUPTION AND REMOVAL OF LUMINAL OCCLUSIONS

CROSS-REFERENCE TO RELATED APPLICATION

The present application claims the benefit of U.S. Provisional Application Ser. No. 60/470,067, filed May 12, 2003, which is hereby incorporated by reference herein in its entirety, including any figures, tables, nucleic acid sequences, amino acid sequences, or drawings.

BACKGROUND OF THE INVENTION

The blockage of human arteries can lead to a variety of serious medical complications. Arterial blockages reduce blood flow through the affected artery and may result in damage to the tissue that is relying upon the blood's supply of oxygen (ischemia). For example, if the blockage is in an artery that supplies blood to the heart itself, a heart attack may result.

Thrombosis and atherosclerosis are common ailments that result from the deposition of thrombus on the walls of blood vessels. When such deposits harden, they are commonly referred to as plaque. These plaque deposits occur commonly in blood vessels that feed the brain, heart, and limbs of the human body. Stasis, incompetent valves, and trauma in the venous circulation are common causes of thrombosis, which can often manifest as a deep vein thrombosis in the peripheral vasculature. When such deposits build-up in localized regions of the blood vessel, they can restrict blood flow and cause a serious health risk.

In addition to forming in the natural vasculature, thrombosis is a serious problem in "artificial" blood vessels, particularly in peripheral femoral-popliteal and coronary bypass grafts and dialysis access grafts and fistulas. The creation of such artificial blood vessels requires anastomotic attachment at one or more locations in the vasculature. Such sites are particularly susceptible to thrombus formation due to narrowing caused by intimal hyperplasia, and thrombus formation at these sites is a frequent cause of failure of the implanted graft or fistula. The arterio-venous grafts and fistulas that are used for dialysis access are significantly compromised by thrombosis at the sites of anastomotic attachment and elsewhere. Thrombosis often occurs to such an extent that the graft needs to be replaced within a few years or even a few months.

A variety of methods have been developed for treating thrombosis and atherosclerosis in the coronary and peripheral vasculature as well as in implanted grafts and fistulas. Such techniques include pharmacologic thrombolytic therapy, given either intravenously or intra-arterially (Hacke W. et al., *JAMA*, 274:1017-1025, 1995; del Zoppo G. J. et al., *Stroke*, 29:4-11, 1998), surgical procedures, such as coronary artery bypass grafting, and minimally invasive procedures, such as angioplasty atherectomy, transmyocardial and revascularization. In particular, a variety of techniques generally referred to as "thrombectomy" have been developed. Thrombectomy generally refers to procedures for the removal of relatively soft thrombus and clot from vasculature. Removal is usually achieved by mechanically disrupting the clot, and can optionally include the administration of thrombolytic agents. The disrupted thrombus or clot is then withdrawn through a catheter, typically with a vacuum or mechanical transport device.

Thrombectomy generally differs from angioplasty and atherectomy in the type of occlusive material that is being treated and in the level of care taken to avoid damage to the blood vessel wall. The material removed in most thrombectomy procedures is relatively soft, such as the clot formed in deep vein thrombosis, and is usually not hardened plaque of the type treated by angioplasty in the coronary vasculature. Moreover, it is usually an objective of thrombectomy procedures to have minimum or no deleterious interaction with the blood vessel wall. Ideally, the clot will be disrupted and pulled away from the blood vessel wall with no harmful effect on the wall itself.

While successful thrombectomy procedures have been achieved, most have required compromise between the competing objectives of removing the thrombosis and minimizing injury to the blood vessel wall. While more aggressive thrombectomy procedures employ rotating blades that can be very effective at thrombus removal, they present a significant risk of injury to the blood vessel wall. Alternatively, those procedures that rely primarily on vacuum extraction together with minimum disruption of the thrombus, often fail to achieve sufficient thrombus removal.

U.S. Pat. No. 5,904,698 describes a catheter having an expandable mesh with a blade or electrode for shearing obstructive material, which penetrates the mesh when the mesh is expanded in a blood vessel. Other catheters having expandable meshes, cages, and/or shearing elements are described in U.S. Pat. Nos. 5,972,019; 5,954,737; 5,795,322; 5,766,191; 5,556,408; 5,501,408; 5,330,484; 5,116,352; and 5,410,093; and WO 96/01591. Catheters with helical blades and/or Archimedes screws for disrupting and/or transporting clot and thrombus are described in U.S. Pat. Nos. 5,947,985; 5,695,501; 5,681,335; 5,569,277; 5,569,275; 5,334,211; and 5,226,909. Other catheters of interest for performing thrombectomy and other procedures are described in U.S. Pat. Nos. 5,928,186; 5,695,507; 5,423,799; 5,419,774; 4,762,130; 4,646,736; and 4,621,636. Techniques for performing thrombectomy are described in Sharafudin et al. (*JVIR* 8:911-921, 1997) and Schmitz-Rode et al. (*Radiology* 180:135-137, 1991).

One of the problems with many of these devices, however, is that particulate matter (e.g., thrombus, atheroma, or other embolic or occlusive material) may be released from the wall of the vessel during the procedure. If such particulate matter travels downstream, it may become lodged or otherwise harm the patient. For example, ischemic stroke may occur when such emboli are released in the carotid or cerebral arteries and travel to the patient's brain. To prevent or minimize damage from emboli, vascular filters have been suggested that are typically disposed on a device such as a catheter, guidewire, or sheath. These devices may be introduced within a blood vessel downstream of a location being treated, and the filter on the device deployed across the vessel to capture embolic material released during the procedure. Upon completion of the procedure, the filter may be collapsed, trapping emboli therein, and then the device may be removed from the patient. Catheters having expandable filters at their distal ends are described in U.S. Pat. No. 4,928,858 and PCT publications WO99/44542 and WO99.44510.

The United States Food and Drug Administration (FDA) has approved a total of eight mechanical thrombectomy devices (MTDs) for use in thrombosed hemodialysis grafts (Kasirajan K. et al., *J. Vasc. Interv. Radiol.*, 2001, 12:405-411). Generally, the approved MTDs can be classified into two categories: (i) mechanical lysis only (non-aspirating) devices and (ii) mechanical and aspirating devices. The AMPLATZ thrombectomy device (CLOT BUSTER; MICROVENA, White Bear Lake, Minn.), ARROW-TRERO-TOLA PTD (ARROW INTERNATIONAL, Reading, Pa.), and CASTANEDA OVER-THE-WIRE BRUSH (MICRO THERAPEUTICS, Aliso Viego, Calif.) are categorized mechanical non-aspirating devices and ANGIOJET (POSSIS MEDICAL; Minneapolis Minn.), GELBFISH-ENDOVAC (BOSTON SCIENTIFIC/MEDI-TECH, Brooklyn, N.Y.), HYDROLYSER (CORDIS, Miami, Fla.), OASIS (BOSTON SCIENTIFIC/MEDI-TECH, Watertown, Mass.) are categorized under mechanical aspirating devices. The ANGIOJET LF140 (POSSIS MEDICAL, Minneapolis, Minn.) is the only FDA approved device for use in peripheral arterial occlusive disease. These devices are currently being used or undergoing clinical evaluation for the treatment of acute and chronic limb-threatening ischemia.

Stroke is characterized by a sudden loss of blood supply to the brain, which results in loss of neurological function. Stroke is the third leading cause of death in the United States (150,000 cases per year) and the leading cause of adult disability ("2002 Heart and Stroke Statistical Update", American Heart Association, Dallas, Tex., 2001). Approximately 700,000 strokes occur annually in the U.S., accounting for costs of over $26 billion/year for treatment and rehabilitation. Stroke is currently classified into two categories: hemorrhagic and ischemic. Ischemic stroke is the most common type and accounts for 85% of all stroke cases. Ischemic stroke (i.e., thromboembolic stroke) occurs when arteries supplying blood to the brain are occluded by thrombus or other embolic material (e.g., calcifications, cholesterol, plaque, etc.).

Current treatment modalities include pharmacologic thrombolytic therapy; however, all thrombolytic drugs are not indicated for all stroke victims and are not effective for all thromboembolic occlusions. The treatment of ischemic stroke patients with tissue plasminogen activator (tPA) is currently the only FDA approved treatment in the United States. However, tPA has been shown to benefit patients only if administered within a 3 hour time window after the onset of neurological symptoms. Therefore, a poor success rate in treatment of stroke is observed. Moreover, the use of tPA is associated with a high risk of hemorrhage and cannot be given to all patients. Endovascular mechanical thrombolytic devices could be used to treat ischemic stroke patients less invasively and more effectively. Unfortunately, there currently exists no FDA approved device for ischemic stroke treatment. Mechanical thrombectomy devices may increase the risk of arterial perforation, dissection, or endothelial injury, which can result in intracranial hemorrhage and worsening of neurological deficits, for example. Therefore, making such devices that will eliminate or even reduce these risks is an extremely challenging task. For example, a device adapted to treat ischemic stroke should be miniaturized to fit inside intracranial arteries, which are relatively small (1 mm to 3.5 mm in diameter). Intracranial arteries are fragile and tortuous; therefore, the device should also be highly flexible and maneuverable. The use of such devices, along with tPA, may benefit patients by providing a quick recovery from ischemic stroke.

Preliminary studies on the safety, efficacy, and device limitations have spurred an interest in percutaneous techniques for thrombus debulking as stand-alone therapy or as an adjunct to pharmacologic thrombolysis. The devices have various mechanisms or combinations of mechanisms to optimize thrombus removal. Efficacy of thrombus removal is balanced by the propensity for vessel wall damage and distal embolization, especially for vessel wall-contact devices.

Therefore, there is a need for a device that is simple in design and is highly maneuverable to permit navigation through various lumen systems of the body, such as the intracranial, urinary, biliary, bronchial, and coronary systems, thereby facilitating effective disruption and removal of occlusive material while minimizing the risk of injury to the lumen wall.

BRIEF SUMMARY OF THE INVENTION

The subject invention concerns a device and methods for disrupting and/or removing occlusive material from lumens, such as biological lumens within the body. Although the subject invention is particularly useful for the disruption and/or removal of thrombus from the vasculature, it is also applicable in other lumens of the body, such as the ureter, urethra, fallopian tubes, bile duct, intestines, and the like. The subject invention provides for effective disruption and/or removal of the occlusive material from the body lumen with minimal risk of injury to the lumen wall. Advantageously, the invention can be used to achieve a high degree of removal while minimizing the amount of occlusive material that is released into the body lumen. This is particularly desirable in treatment of the vasculature, where the release of emboli can be a serious risk to the patient. As described in detail below, the present invention employs a cutting means for disrupting the thrombus, clot, embolic agent, or other occlusive material.

The present invention relates to an elastic sheath used for constructing occlusion disruption and/or removal devices of the invention (also referred to herein as a "thrombectomy device" or "thrombolysis device"). The present invention further relates to a device for occlusion removal and/or disruption comprising a rod, an elastic sheath that ensheaths a segment of the rod, wherein the sheath has a plurality of slits, and means for expanding the elastic sheath, wherein the elastic sheath is displaced from the segment of the rod when the expansion means is activated, and wherein the rod, the expansion means, and the elastic sheath cooperate structurally and/or functionally to form a compartment when the expansion means is activated. Preferably, the expansion means is an expandable balloon and the elastic sheath covers at least a portion of the expandable balloon and at least a segment of the rod adjacent to the expandable balloon.

The elastic sheath has a plurality of slits, with each slit separated from the adjacent slit by a band of elastic material. When the expansion means is activated, the slits expand and a compartment (also interchangeably referred to herein as the "cage") is formed through the cooperation of the rod, the elastic sheath, and the expansion means, together. When the expansion means is an expandable balloon, the balloon can be expanded by applying pressure from within the balloon, such as air or saline pressure, for example. The device can be at least partially composed of an imageable material such that the position of the device within biological tissue, such as a biological lumen, can be readily determined using the appropriate sensing equipment. Therefore, it is possible to accurately guide the device to a particular lumen within biological tissue, and to guide the device to an occluded area within the lumen for subsequent disruption and/or removal of the occlusive material.

In another aspect, the subject invention pertains to a method for disrupting and/or removing occlusive material from a biological lumen by inserting the device of the invention into the lumen, placing the device at a point adjacent to the occlusion, activating the expansion means, and operating the device in a back-and-forth motion such that the occlusion is mechanically disrupted by abrasive contact with the bands of the elastic sheath, and occlusive debris passes through the expanded slits, and is thereby captured within the cage of the elastic sheath. Optionally, the expansion means can be deactivated in order to narrow or close the slits (collapsing the cage), to more securely contain the occlusive debris between the bands of the elastic sheath and the rod. In embodiments where the expansion means is an expandable balloon, the balloon can be partially or entirely deflated in order to narrow or close the slits and collapse the cage around the rod.

In another aspect, the present invention concerns an in vitro model of luminal occlusion and methods for using the in vitro model to test the efficacy of devices and methods for treating luminal occlusions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 2A, the unconstrained portion of the balloon is disposed toward the distal end of the rod. In FIG. 2B, the unconstrained segment of the balloon is disposed toward the central portion of the rod. In FIG. 2C, two unconstrained segments of the balloon are disposed toward the central portion of the rod, adjacent to one another.

FIG. 4A shows a device with one balloon, in an expanded configuration, disposed toward the distal end of the rod. FIG. 4B shows a device with one balloon, in an expanded configuration, disposed toward the central portion of the rod. FIG. 4C shows two balloons, in expanded configurations, disposed toward the central portion of the rod.

FIG. 7A shows a polypropylene tube of 2.5 mm inner diameter (ID). FIG. 7B shows a clot holder that is a detachable silicone pouch with two openings. The clot holder is attached to the polypropylene tube through plastic fittings.

DETAILED DISCLOSURE OF THE INVENTION

Figure 1A:
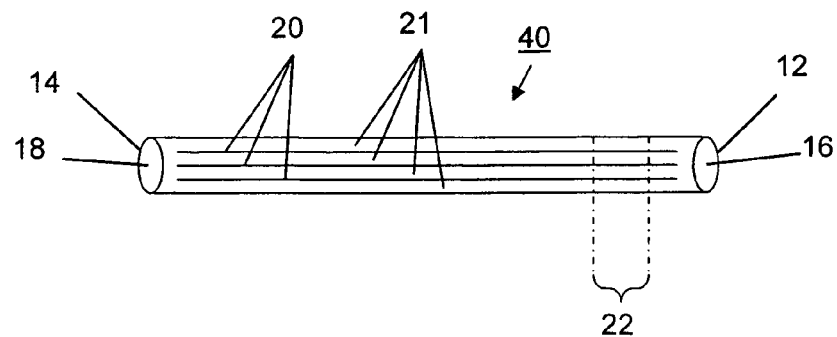
FIG. 1A shows a side view of an elastic sheath constructed in accordance with the present invention, with the placement site of the balloon within the distal end of the elastic sheath. When this embodiment of the elastic sheath is utilized, one conical cage structure can be formed when the underlying balloon is activated at the balloon site shown.

The subject invention concerns a device and methods for disrupting and/or removing occlusive material from lumens, such as a blood vessel, ureter, urethra, fallopian tube, bile duct, intestine, and the like. In addition to biological conduits, the device and methods of the present invention can be utilized to disrupt and/or remove occlusive materials from artificial conduits, such as those constructed for insertion into the body (e.g., arterial or venous catheters). Where reference is made herein to the "thrombectomy device" of the subject invention, it should be understood that the device can be used to disrupt and/or remove occlusive material from any lumen, biological or artificial.

The thrombectomy device 10 of the present invention has a rod 24, an elastic sheath 40 that ensheaths at least one segment of the rod 24, and means for radially expanding the elastic sheath 40 around the segment of the rod 24. Preferably, the expansion means is at least one expandable balloon 30. In this embodiment, the thrombectomy device 10 of the present invention comprises the rod 24, at least one expandable balloon 30 disposed along the length of the rod 24, the elastic sheath 40 that covers at least a portion of the expandable balloon 30 and ensheaths at least one segment of the rod 24 adjacent to the balloon 30. Preferably, the rod 24, balloon 30, and elastic sheath 40, are co-axial.

Preferably, the means for expanding the elastic sheath 40 radially about the rod 24 is an expandable balloon 30. However, other means for applying sustained radial pressure to the inner surface of the elastic sheath 40, thereby expanding the elastic sheath 40 radially about the rod 24, can be utilized. For example, expansion means can include radially outwardly biased struts. In a deactivated state, the biased struts can be retained within or outside the rod 24. Upon activation, the struts are moved radially outwardly against the inner surface of the elastic sheath 40, thereby expanding the elastic sheath 40 and deploying the cage 50 (see, for example, U.S. Pat. No. 5,911,734, Tsugita et al., which describes a filter and strut structure). In a further embodiment, a compressive spring may be employed which pulls fore and aft ends of expandable struts together, thereby expanding the elastic sheath 40. In other words, the elastic sheath 40 is spring activated. Alternatively, the elastic sheath 40 can be expanded by a radially expandable frame structure comprising frame struts (see, for example, U.S. Pat. No. 6,277,139, Levinson et al., which describes a frame structure attached to perforated filter material).

The elastic sheath 40 has a plurality of slits 20, with each slit 20 separated from the adjacent slit 20 by a band 21 (or string) of elastic material. The slits 20 can be on one side of the expansion means, proximal or distal to the expansion means, or on both sides of the expansion means, proximal and distal to the expansion means. When the expansion means is activated to radially expand the elastic sheath 40 about the rod 24, a portion of the elastic sheath 40 will be displaced from a segment of the rod 24 that it previously ensheathed, the slits 20 expand, forming a compartment 50 (also interchangeably referred to herein as the cage 50 or cage structure 50) around the rod 24. Thus, in embodiments where an expandable balloon 30 is the expansion means, when the balloon 30 is radially expanded about the rod 24 via internal pressure, such as air pressure or saline pressure, portions of the elastic sheath 40 that are adjacent to the balloon 30 are displaced from the rod 24, and the slits 20 expand, forming a roughly cone-shaped compartment 50 around the rod 24.

As used herein to describe the cage 50 of the subject invention, the terms "cone-shaped", "conical", and "frustoconical" are intended to include shapes that linearly, parabolically, or hyperbolically taper from the expansion means (such as the balloon 30) down the length of the rod 24. Any expansion means that radially expands the elastic sheath 40 to cooperate with the rod 24 in forming the cage 50 is sufficient. The conical body of the cage 50 extends (at its broadest point) expansion means to a proximal or distal point (its narrowest point) on the rod 24, as shown in FIGS. 4A-4C and FIG. 5. Therefore, one end of the cage 50 is enlarged in diameter when the expansion means is activated and the elastic sheath 40 is displaced radially (outwardly from the rod 24), and the other end of the cage 50 tapers to the rod 24, away from the expansion means. In this way, in those embodiments wherein the expansion means is one or more expandable balloons 30, the cage 50 of the thrombectomy device 10 is "balloon-activated". When the expansion means is not activated, the elastic sheath 40 (and, hence, the longitudinal bands 21) is in a position of repose (collapsed) in which it is preferably substantially flush with the rod 24. The conical cage 50 can be a unilateral cage, forming on one side of the expansion means, or a bilateral cage, forming on both sides of the expansion means. If the expansion means is a continuously solid structure, such as an expandable balloon 30, the bilateral cages will be separated by the expansion means. However, the expansion means can be a discontinuously solid structure, having voids through which the cages would be in communication.

The rod 24 of the device 10 is preferably highly flexible to facilitate navigation through tortuous biological lumens. The rod 24 can be hollow or solid, and can be composed of one or more of a variety of materials, such as melt-processible and/or non-melt-processible fluoropolymers (e.g., perfluoroalkoxy (PFA); fluorinated ethylene propylene (FEP); poly (tetrafluoroethylene) (PTFE); tetrafluoroethylene (MFA); ethylene tetrafluoroethylene (ETFE); poly(vinylidene fluoride) (PVDF); ethylene chlorotrifluoroethylene (ECTFE); and poly(tetrafluoroethylene-co-perpropylvinylether) (PTFE/PPVE)); polyurethane; polyethylene; nylon; PEBAX, polyvinylchloride (PVC); thermoplastic elastomers; polyesters; and radio-opaque and non-radio-opaque resin blends. If the rod 24 is composed of one or more polymers, the rod 24 can optionally include one or more fillers, such as barium sulfate ($BaSO_4$), bismuth trioxide ($Bl_2O_3$), bismuth subcarbonate ($Bl_2CO_3$), and tungsten (W). Optionally, the rod 24 can include braided wire for enhanced torque capabilities, as long as the rod is sufficiently flexible and kink-resistant for the particular application. Braid wire density, which is described as picks per inch (PPI), i.e., the number of wire crossovers per inch of rod, can be optimized by those skilled in the art. The rod 24 can have any of a variety of shapes in cross-section. Preferably, the rod 24 has a substantially circular cross-section. The length and diameter of the rod 24 will depend on the diameter of the lumen and the target site. For example, the length of the rod 24 can be within the range of about 50 centimeters to about 300 centimeters for many applications, and from about 2.5 F (french) to about 10 F in diameter. Preferably, the length of the rod 24 is about 150 centimeters and the diameter of the rod 24 is about 0.25 millimeters.

The elastic sheath 40 has the general shape of a tube, with a first end 12 with an opening 16 and a second end 14 with an opening 18. When the device 10 is assembled, the rod 24 runs through the openings 16, 18 of the elastic sheath 40.

Preferably, the elastic sheath 40 is produced from an extremely flexible, tear-resistant, biocompatible polymer tube, which can be composed of any of a variety of commercially available thermoplastic elastomers. For example, in order to produce the elastic sheath 40, slits 20 can be made in polymer tubes composed of any of a variety of materials, such as silicone, polyurethane, silicone-polyurethane copolymer, styrene-ethylene-butylene-styrene (copolymer), and other suitable elastomeric materials. The elastic sheath 40 should be sufficiently flexible and resilient such that when a radial force is applied outward from within the sheath 40 (e.g., by the expanding balloon 30), the elastic sheath 40 will expand at the point the force is applied, but will have sufficient memory to revert to its regular tubular shape when the force is removed.

The elastic sheath 40 has a plurality of slits 20. The slits 20 can be uniformly spaced from one another or non-uniformly spaced from one another. Preferably, the slits 20 are longitudinally arranged around at least a portion of the circumference of the elastic sheath 40, or around entire circumference of the elastic sheath 40. However, the slits 20 can be arranged non-longitudinally on the elastic sheath 40. For example, the slits 20 can be arranged at a diagonal relative to the length of the sheath 40. The slits 20 are preferably substantially parallel to one another. In one embodiment, the slits 20 are arranged transverse to the length of the sheath 40. In another embodiment, the slits 20 are arranged non-transverse to the length of the sheath 40.

In one embodiment, the elastic sheath 40 has within the range of 2 to 12 slits 20 proximal to the expansion means. In another embodiment, the elastic sheath 40 has within the range of 2 to 12 slits 20 distal to the expansion means. In another embodiment, the elastic sheath 40 has within the range of 2 to 12 slits 20 both proximal and distal to the expansion means.

The elastic sheath 40 preferably has a length within the range of about 5 millimeters and about 5 centimeters, and a diameter within the range of about 1 millimeter and about 1 centimeter. Preferably, the elastic sheath 40 has a thickness within the range of about 0.05 millimeters and about 2 millimeters.

Figure 1B:
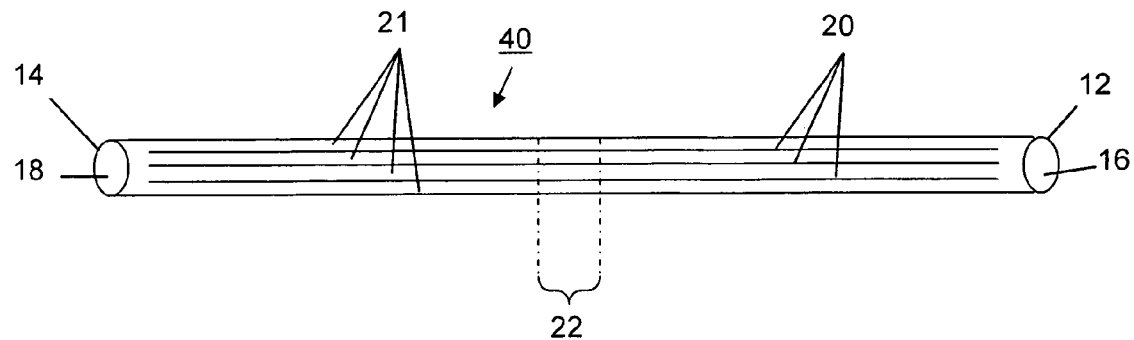
FIG. 1B shows a side view of an elastic sheath constructed in accordance with the present invention, with the placement site of the balloon within the central portion of the elastic tube. When this embodiment of the elastic sheath is utilized, two conical cage structures can be formed when the underlying balloon is expanded at the balloon site shown.

FIG. 1A shows a side view of an elastic sheath 40 constructed in accordance with the present invention, with the placement site 22 of the balloon 30 within the distal end of the elastic sheath 40. When this embodiment of the elastic sheath 40 is utilized, one conical cage structure 50 can be formed when the underlying balloon 30 is activated at the balloon site 22 shown. In FIG. 1A, the longitudinal slits 20 extend from an area of the elastic sheath 40 in close proximity to the balloon 30 and the first end 12 of the elastic sheath 40, to the second end 14 of the elastic sheath 40, permitting formation of the conical cage 50 that extends from the balloon 30 to the point where the longitudinal slits 20 terminate. FIG. 1B shows a side view of an elastic sheath 40 with the placement site 22 of the balloon 30 within the central portion of the elastic sheath 40. When this embodiment of the elastic sheath 40 is utilized, two conical cage structures 50 can be formed (proximal and distal to the balloon 30) when the underlying balloon 30 is expanded at the balloon site 22 shown.

Figure 2A:
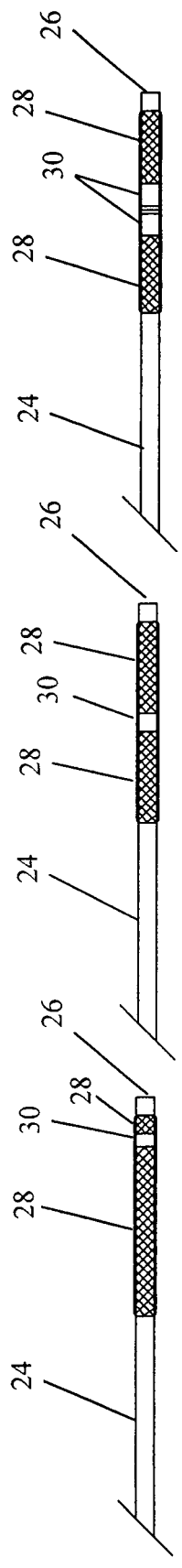
FIGS. 2A-2C show side views of a rod constructed in accordance with the present invention, with a balloon disposed along the length of the rod and constraining material wrapped around opposing segments of the balloon and adjacent segments of the rod, leaving a segment of the balloon unwrapped and, hence, capable of expansion.
Figure 2B:
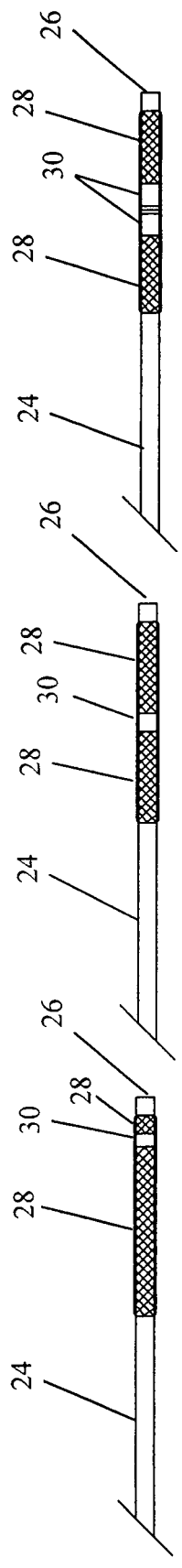
Figure 2C:
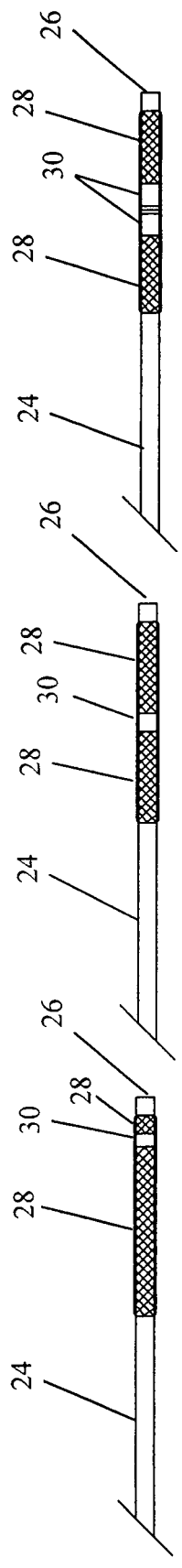

FIGS. 2A-2C show side views of a rod 24 constructed in accordance with the present invention, with a balloon 30 disposed along the length of the rod 24 and constraining material 28 wrapped around opposing sides of the balloon 30 and adjacent segments of the rod 24, leaving the unconstrained segment of the balloon 30 capable of expansion. In FIG. 2A, the unconstrained segment of the balloon 30 is disposed toward the distal end 26 of the rod 24 and toward the distal end of the elastic sheath 40. In FIG. 2B, the unconstrained segment of the balloon 30 is disposed more toward the central portion of the rod 24 (as compared to FIG. 2A) and approximately in the center of the elastic sheath 40. In FIG. 2C, two unconstrained segments of the balloon 30 are disposed toward the central portion of the rod 24, adjacent to one another, and approximately in the center of the elastic sheath 40. In an alternative embodiment, instead of leaving two or more segments of a single balloon unconstrained, two or more separate balloons 30 can be utilized.

Figure 3A:
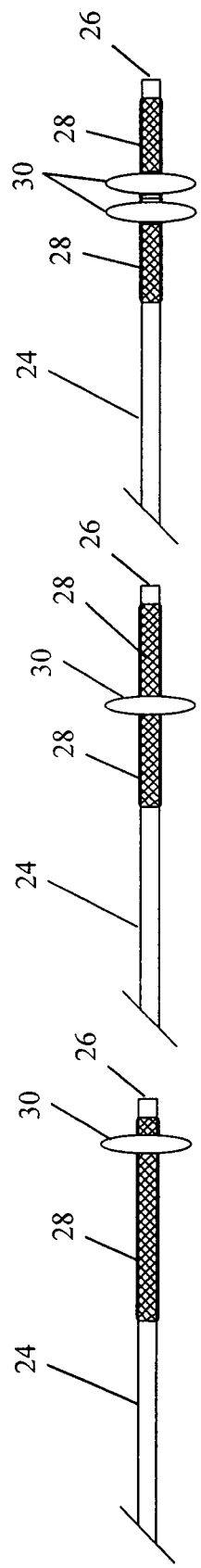
FIGS. 3A-3C show side views of the rods shown in FIGS. 2A-2C, respectively, with the balloon expanded.
Figure 3B:
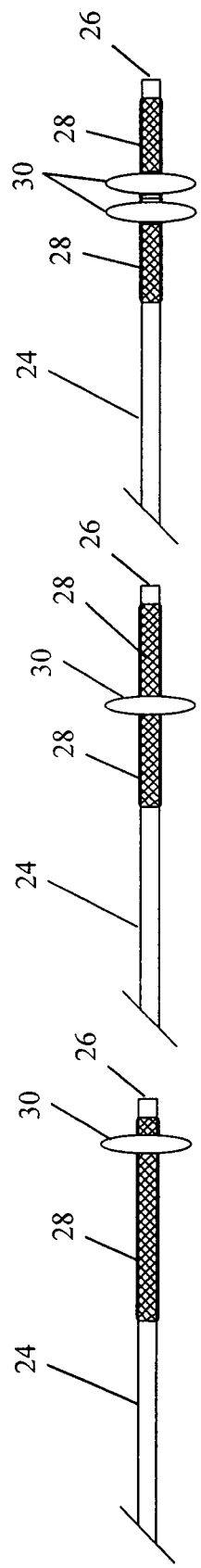
Figure 3C:
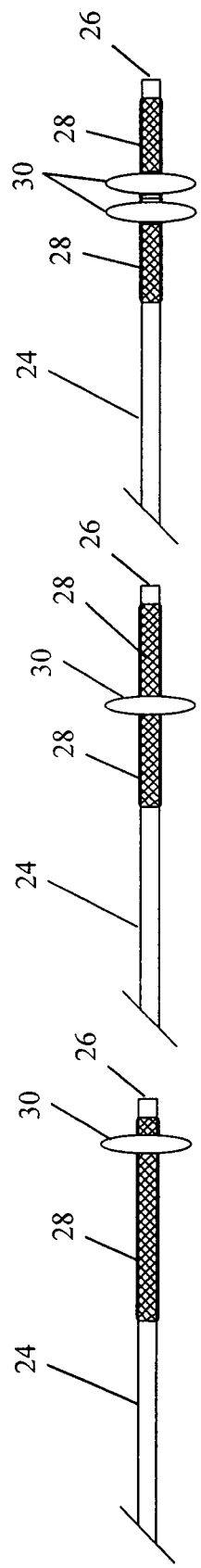
Figure 4A:
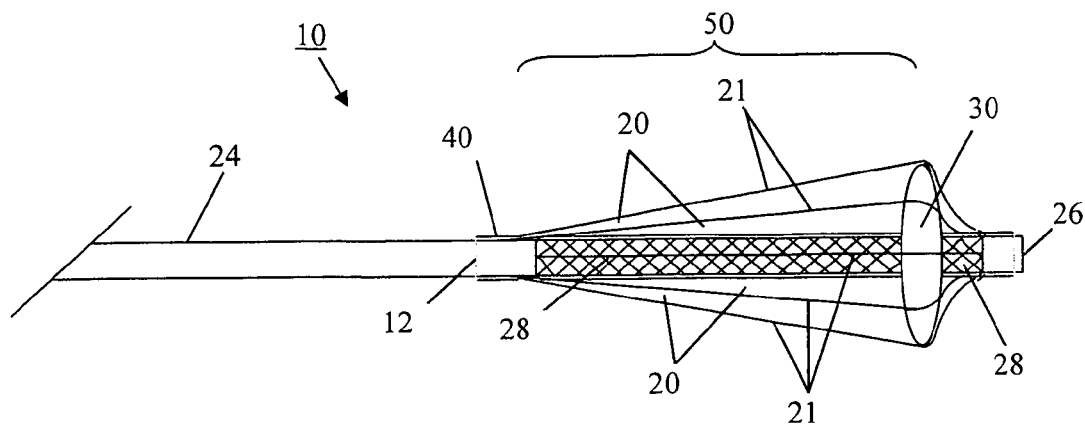
FIGS. 4A-4C show side views of devices of the subject invention in an expanded configuration.
Figure 4B:
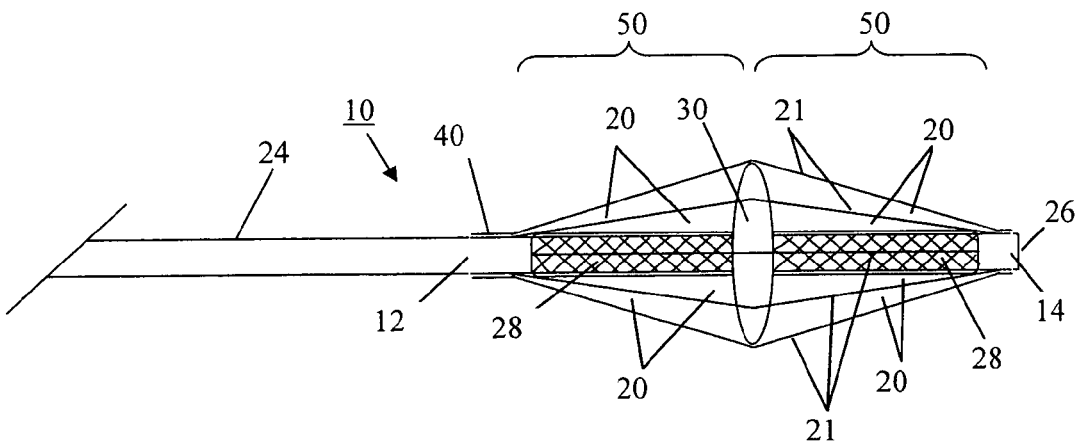
Figure 4C:
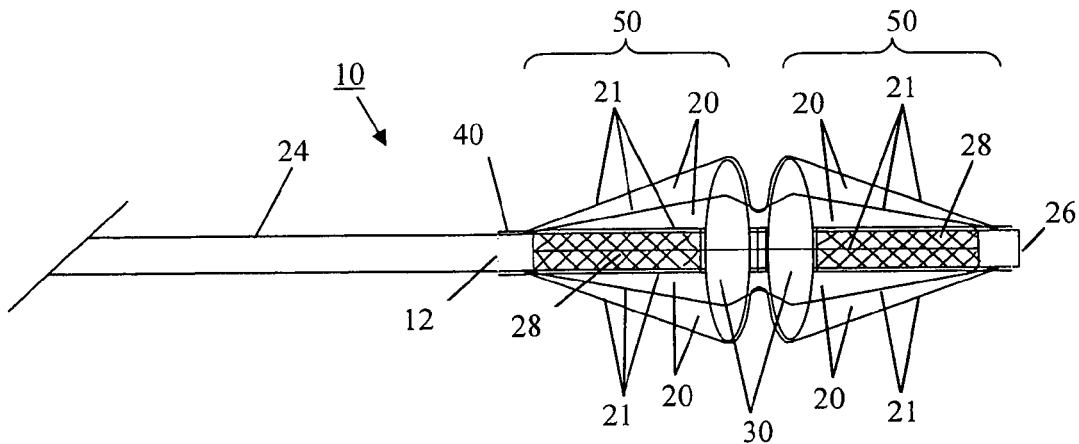

FIGS. 3A-3C show side views of the rods shown in FIGS. 2A-2C, respectively, with the balloons 30 expanded. FIGS. 4A-4C show three embodiments of the device 10 in an expanded configuration (i.e., with the cage 50 deployed). As shown in FIG. 4A, the elastic sheath 40 can be placed on the rod 24 such that the expandable balloon 30 is off center relative to the length of the elastic sheath 40. In this way, the size of the expanded cage 50 can be varied. Further, as shown in FIG. 4B, the elastic sheath 40 can be placed on the rod 24 such that the expandable balloon 30 is approximately in the center of the elastic sheath 40, which provides two cages 50 when then the device 10 is in an expanded configuration (the balloon 30 is expanded). FIG. 4C demonstrates that the device 10 may comprise a balloon 30 with two or more unconstrained segments (also shown in FIG. 2C, unexpanded and without the elastic sheath 40; and in FIG. 3C, expanded and without the elastic sheath 40). Alternatively, instead of leaving two or more segments of a single balloon unconstrained, two or more individual balloons 30 can be utilized.

Figure 5:
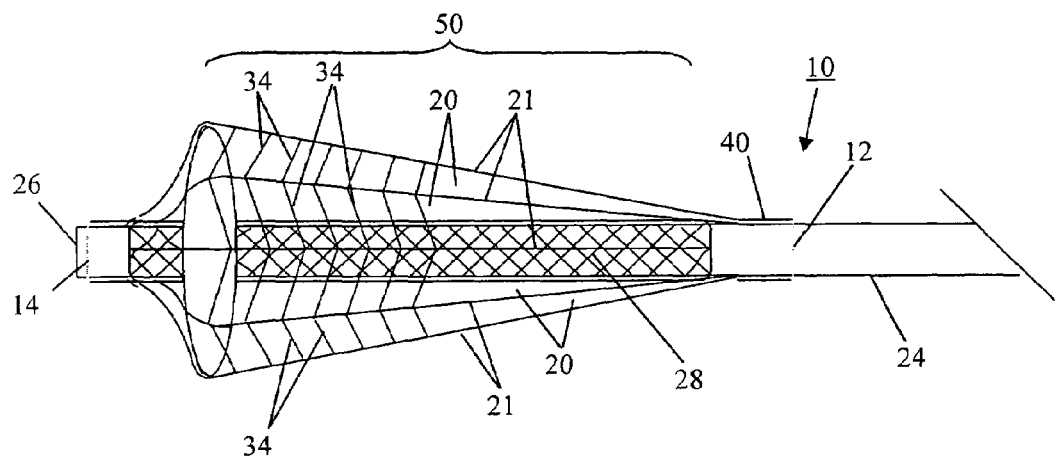
FIG. 5 shows a side view of one embodiment of the device of the invention, in an expanded configuration, with lateral bands cross-linking the longitudinal bands, to produce a mesh.

FIG. 5 shows a side view of one embodiment of the device 10 of the invention, in an expanded configuration, with lateral bands 34 cross-linking the longitudinal bands 21 such that the expanded cage 50 resembles a mesh. The lateral bands 34 can bridge longitudinal bands 21 at any of a variety of acute, obtuse, or right angles relative to the longitudinal bands 21 which they interconnect. When the device 10 is operated, the lateral bands 34 function to shear the occlusive material and enhance the ability of the cage 50 to retain disrupted occlusive debris. The lateral bands 34 can be formed integrally within the elastic sleeve 40, in a similar fashion as the longitudinal bands 21. Alternatively, the lateral bands 34 can be subsequently added and secured to the longitudinal bands 21.

Figure 11:
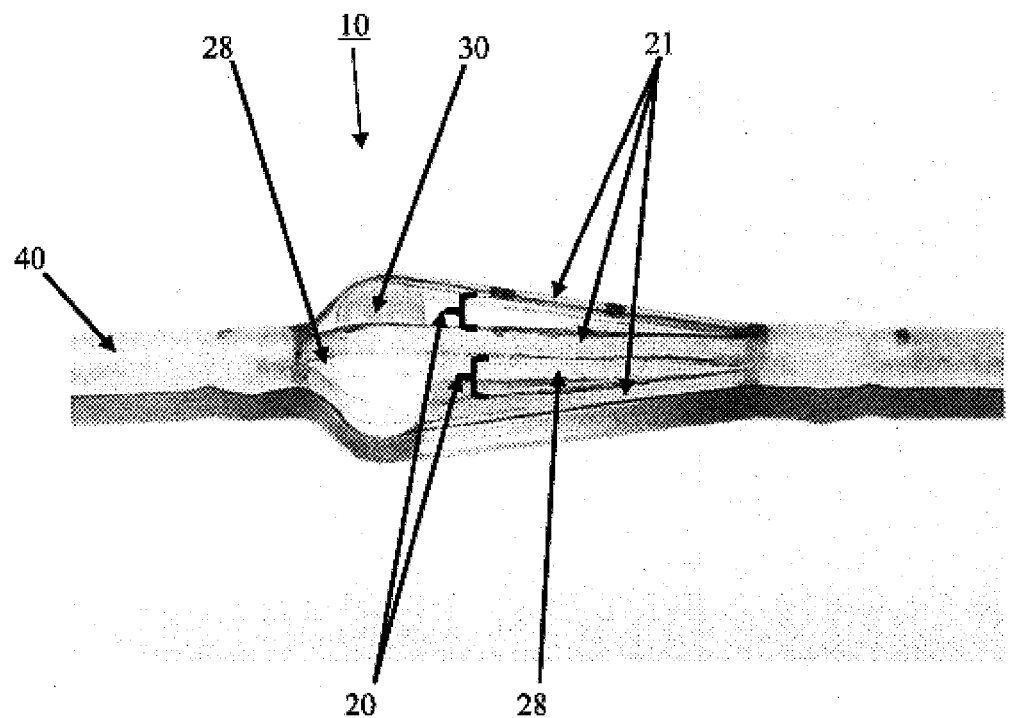
FIG. 11 shows a side view photograph of a device constructed in accordance with the present invention.
Figure 12:
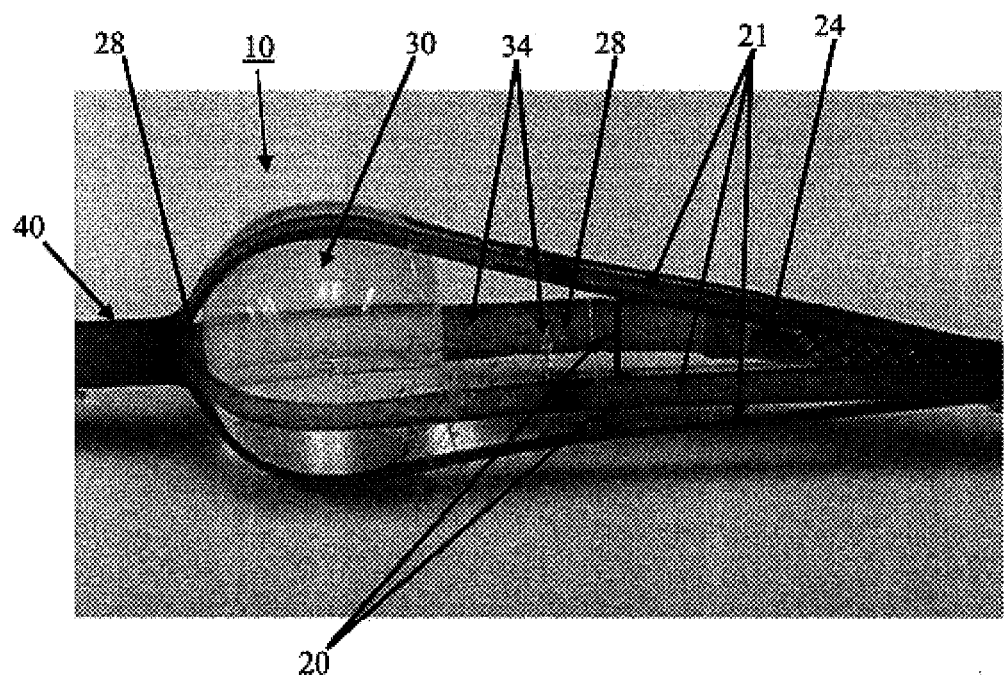
FIG. 12 shows a side view photograph of another embodiment of the device constructed in accordance with the present invention, with lateral bands cross-linking the longitudinal bands.

Preferably, the expandable balloon 30 is spherical or substantially spherical such that, when the balloon 30 is expanded, a "cage" is formed. However, the balloon 30 can be any shape which, when expanded, also stretches and expands the longitudinal slits 20 and longitudinal bands 21, permitting sufficient disruption of occlusive material and, preferably, capture by the cage 50. For example, the expandable balloon 30 can be ring-shaped, permitting blood flow through the hole of the ring. Preferably, the balloon 30 is disposed concentrically around a portion of the rod 24, as shown in FIGS. 11 and 12, or at its distal end 26. When the device 10 is in an expanded configuration, the balloon 30, cage 50, and the rod 24 define a holding compartment to collect and hold occlusive debris material. The balloon 30 can be arranged on the rod 24 in any of a variety of ways permitting expansion of the balloon 30 and formation of the cage 50 defining the holding compartment, including many balloon-catheter arrangements known in the art (e.g., FOGARTY embolectomy catheter; SENTRY balloon catheter; EQUINOX occlusion balloon system; U.S. Pat. Nos. 3,435,826; 5,824,037; 4,762,130; 5,250,029; 4,403,612; 3,467,101; 5,232,445; 4,919,651; 4,637,396). The balloon 30 can be mounted longitudinally or transversely on the rod 24, for example. Appropriate means for expanding the balloon 30, such as by applying internal pressure to the balloon 30, can likewise be employed. For example, the rod 24 can include one or more openings along its length that are in fluid communication with the interior of the balloon 30, permitting passage of fluid (e.g., gas or liquid) between the interior of the hollow rod 24 and the interior of the balloon 30, as described in U.S. Pat. No. 3,435,826. The rod 24 of the device 10 can include concentric or non-concentric interior lumens or an external tube connecting the balloon 30 to an external source of pressurized fluid. The expandable balloon 30 can be composed of any of a variety of materials. Preferably, the balloon 30 is a biocompatible elastic material, such as synthetic or natural rubber latex, silicone, polyurethane, polyisoprene styrene-ethylene-butylene-styrene block copolymer (SEBS), or other suitable elastomeric material.

At least a portion of the balloon 30 can be radially constrained, leaving at least one portion of the balloon 30 radially unconstrained. In this way, when pressure is applied to the constrained balloon 30, the unconstrained portion or unconstrained portions of the balloon 30 expand but the constrained portion or portions do not. In one embodiment, an elongated, tube-shaped balloon 30 is utilized (such as an angioplasty balloon), wherein the balloon 30 is radially constrained at either or both ends, leaving one or more segments of the balloon 30 unconstrained. In this way, when pressure is applied to the constrained balloon 30, the unconstrained segment or unconstrained segments of the balloon 30 preferably expand to form a sphere or substantially spheroid shape. The radial constraint can be provided in any of a number of ways. For example, radial constraint can be provided by a constraining material 28 that surrounds and radially constrains portions of the balloon 30 (e.g., segments of the balloon 30 at either or both ends). The constraining material 28 prevents those portions of the balloon 30 that the constraining material 28 surrounds from expanding, leaving the rest of the balloon 30 (e.g., the center portion of the balloon 30) capable of full expansion. For example, the constraining material 28 can be a fiber, such as polyurethane fiber (e.g., SPANDEX), that is wrapped around those portions of the balloon 30 to be constrained.

When the balloon 30 is expanded, the balloon 30 preferably has a diameter within the range of about 1 millimeter to about 3 centimeters, and a length within the range of about 1 millimeter to about 1 centimeter. Preferably, the thickness of the balloon 30 is within the range of about 0.01 millimeter and about 0.5 millimeter.

The thrombectomy device 10 of the present invention is particularly useful for treating vascular thrombosis and pathological conditions associated with vascular thrombosis, such as ischemic thromboembolic stroke. Because the device 10 of the subject invention can be constructed so as to be highly flexible and maneuverable, the device 10 will be suitable for operation in previously inaccessible anatomical regions, such as intracranial, urinary, biliary, bronchial, coronary, or other physiological lumen systems. Due to its elastic property, the cage 50 can be expanded and contracted multiple times to obtain optimal size and position before it is used to retrieve occlusive debris. Because of the soft, elastic property of the longitudinal bands 21 of the sheath 40, the device 10 will cause minimal trauma to the endothelial cellular layer.

Advantageously, the size of the cage can be controlled. The cage is formed only when the balloon is deployed by pressure. The higher the pressure applied to the balloon, the larger the cage's size. In addition, it will be possible to work with a variety of lumen sizes with the same device.

In another aspect, the subject invention pertains to a method for disrupting and/or removing occlusive material from a biological lumen, such as a blood vessel. The for sake of simplicity, the method will be described wherein the expansion means is an expandable balloon 30. However, other means for expanding the elastic sheath 40 to form the cage 50 can be utilized. The method is carried out by inserting the device 10 of the invention into the lumen, placing the expandable balloon 30 and cage 50 at a target site within or adjacent to the occlusion, expanding the balloon 30, and operating the device in a back-and-forth and, optionally, twisting motion such that the occlusion is mechanically disrupted by shearing contact with the longitudinal bands 21 of the elastic sheath 40, or with the longitudinal bands 21 and lateral bands 34, depending upon the particular embodiment. Advantageously, occlusive fragments and debris material produced by expansion of the balloon 30 against the occlusion and/or shearing contact of the occlusion with the bands 21, pass through the expanded slits 20, and are thereby captured within the cage formed by the expanded elastic sheath 40. Advantageously, although the longitudinal bands 21 of the device 10 may contact the luminal wall, little or no damage to the luminal wall results. Optionally, the balloon 30 can then be partially or entirely deflated, in order to narrow or close the slits 20, thereby more securely containing the disrupted occlusive debris material between the bands 21 of the elastic sheath 40, the balloon 30, and the rod 24. The device 10 is then removed from the patient.

For example, an incision can be made and the device 10 of the subject invention can be inserted through an artery, such as the femoral artery in the patient's groin, and directed to the site of the occlusion. The device 10 can be inserted and positioned at a point in the lumen before, within, or beyond the occlusion. Either end of the device 10 can be inserted first into the lumen, so long as the longitudinal bands 21 and/or lateral bands 34 can make searing contact with the occlusion, thereby disrupting the occlusion and, optionally, providing an opportunity for the expanded cage 50 to capture particles from the disrupted occlusion.

Once the device 10 is in place, the means for expanding the balloon 30 can be activated. For example, the device 10 can be in operable communication with a pump that provides gas or fluid (e.g., saline solution) to the balloon 30. The balloon 30 can be expanded to such an extent that the balloon 30 makes radial contact with the inner walls of the lumen or occlusive material deposited on the luminal walls. Optionally, the balloon 30 can be expanded to such an extent that the lumen becomes dilated, as during angioplasty procedures. Physicians of ordinary skill in the art can determine optimal pressures to be applied to the balloon 30, optimal diameters to which the balloon 30 is to be expanded within the occluded lumen, and durations of balloon 30 expansion. The operator of the device 10 can use a back-and-forth and/or twisting motion in order to facilitate disruption and capture of the occlusive material within the cage 50. The balloon 30 can then be deflated, contracting the cage 50, and the device 10 can be withdrawn from the biological lumen. Preferably, the device 10 is operated such that any occlusive debris freed by the device is maintained proximally of the balloon 30 and the distal rod end 26, thereby minimizing the risk of occlusive debris migrating to a remote site.

Optionally, the thrombolytic device 10 of the subject invention can be used in conjunction with various pharmacologic substances that breakup or dissolve the occlusion, and/or prevent the formation of future occlusions. For example, in the case of blood clots (also known as thrombi), various anticoagulant, thrombolytic (so called "clot-busting" drugs) or anti-platelet agents can be administered orally or intravenously. Examples include heparin (CALCIPARINE, HEPATHROM, LIP-HEPIN, LIQUAEMIN, PANHEPRIN), warfarin (ATHROBMIN-K, PANWARFIN), tissue plasminogen activator (tPA; ALTEPLASE; ACTIVASE), streptokinase (KABIKINASE, STREPTASE), urokinase (ABBOKINASE), anistreplace, aminocaproic acid, aprotinin, acetylsalicylic acid (aspirin), dipyridamole (PERSANTINE), abciximab (CENTOCOR), dalteparin (FRAGMIN), enoxaparin (LOVENOX), hirudin (DESIRUDIN), 4-hydroxycoumarin (COUMADIN), lepirudin (REFLUDAN), protamine sulfate, phytonadione (Vitamin $K_1$), reteplase (RETAVASE), and ticlopidine (TICLID). Many of these agents operate by inhibiting the clotting mechanism (anticoagulants), lysing thrombi (fibrinolytic agents), and interfering with platelet adhesion and/or aggregation.

Various components of the thrombolytic device 10, such as the rod 24, the elastic sheath 40, and/or the expansion means (such as the expandable balloon 30), can be impregnated or coated with one or more biologically active agents, such as pharmacologic substances that breakup or dissolve the particular occlusion to be removed. The biologically active agents can function on contact with the device 10 or the substances can be released from the device 10 into the biological lumen in a controlled release fashion. Optionally, the biologically active agents can be released and/or become activated upon contact with blood, or otherwise be responsive to the physiological environment. For example, the biologically active agents can be temperature-sensitive and/or pH-sensitive. As an alternative to impregnated or coated components, the biologically active agent can be delivered by other means, such as a port on the rod 24 of the device 10 that permits injection of the biologically active agent at a target site. As used herein, the term "biologically active agent" refers to any substance that is capable of promoting or causing a therapeutic effect in a patient.

Methods known in the art for insertion and operation of an angioplasty catheter can also be utilized with the device 10 of the present invention. For example, the device 10 of the present invention can be introduced into a biological lumen through an introducer (also known as an introducing catheter), which is used to access the lumen. Guide wires can also be utilized.

As indicated above, where reference is made herein to the "thrombectomy device" or "thrombolytic device" of the subject invention, it should be understood that these terms are used herein interchangeably and the device can be used to disrupt and/or remove any occlusive material from any lumen, whether the occlusive material and lumen are biological or artificial. For example, in addition to disrupting and, optionally, removing thrombus or other endogenous embolic material, such as calcifications, cholesterol, plaque, etc., from a biological lumen, the device 10 of the present invention can be used to disrupt and/or remove exogenous embolic material, such as embolic agents. Embolic agents that can be disrupted and/or removed with the device 10 of the present invention include, but are not limited to, adhesive (such as polymerizing adhesive), gel, silicone rubbers, urethanes and other organic elastomers, polymerizable protein solutions, silk sutures, polyvinyl alcohol (PVA) particles, cross-linked polyvinyl alcohol foam, polyurethane foam, acrylic polymers, polyethylene foam, silicone foam, fluorinated polyolefin foam, and/or an ethylene-vinyl-alcohol copolymer commercially available under the designation ONYX by MICRO THERAPEUTICS, INC (Irving, Calif.) (Dehdashti, A. R. et al., *Neurosurg. Focus* 11(5):1-6, 2001; Halbach V. V. et al., *AJR* 153:467-476, 1989; Purdy P. D. et al., *J. Neurosurg.* 77:217-222, 1992; Purdy P. D. et al., *Am. J. Neuroradiol.* 11:501-510, 1990).

ONYX is a liquid embolic (or embolization) agent that is a mixture of ethylene-vinyl alcohol copolymer (EVOH), dimethyl sulfoxide (DMSO), and micronized tantalum (to enable visualization under fluoroscopy) that can be used to fill aneurysms. Contact of ONYX with blood results in its solidification from the outside inward, thereby forming a spongy polymeric cast (Jahan R. et al., *Neurosurgery* 48(5):984-997, 2001; Hamada J. et al., *J. Neurosurg.* 97(4):889-895, 2002; Hamada J. et al., *Am. J. Neuroradiol.* 17(10):1895-1899, 1996). The ONYX embolic agent can be used for the treatment of aneurysms and arteriovenous malformations (AVMs), two conditions which can lead to hemorrhagic stroke. Once delivered inside the targeted malformation, the ONYX embolic agent quickly solidifies into a spongy polymer mass designed to seal off the defective portion of the vessel. In aneurysm and AVM applications, the ONYX filling is intended to reduce the risk of rupture and subsequent stroke. The device 10 of the present invention can be used to disrupt and/or remove excess or otherwise undesired ONYX material present within a vessel.

Depending upon the occlusive material to be removed or retrieved, disruption or breaking apart of the occlusive material may not be necessary. For example, where the device 10 of the present invention is used to retrieve embolization devices, such as those used in the field of cardiology for treating aneurysms, no disruption of the embolization device may be necessary and the embolization device may simply be captured with the cage 50 of the device 10 of the present invention and pulled out of the biological lumen. Examples of such embolization devices include, but are not limited to, PVA particles, detachable balloons, and embolization coils. Advantageously, large or small amounts of occlusive material can be removed using the device 10 of the present invention. The occlusive material can be any occlusive or potentially occlusive material that can be dislodged from the luminal wall and/or captured by the cage 50 of the device 10. The occlusive material can be of various phases, such as solid, semi-solid, or liquid.

Optionally, any component of the thrombectomy device 10 of the subject invention can be at least partially composed of an imageable material. For example, the rod 24, balloon 30, and/or elastic sheath 40, can be composed of an imageable material. As used herein, an "imageable material" includes those materials the location of which can be discerned within a given opaque, ambient medium such as biological tissue, using the appropriate sensing equipment, such as imaging equipment. The imageable material selected should have an image "signature" discernibly different from that of the surrounding medium into which the device 10 is to be introduced. Components of the device 10 can be coated or impregnated with one or more imageable materials, for example.

In one embodiment, the imageable material is an echogenic material with an acoustic impedance different from that of the surrounding medium (i.e., high acoustic impedance differential), enabling the thrombectomy device 10 to be imaged using a sonic imaging device (e.g., ultrasound imaging equipment). A variety of materials that are echogenic (i.e., sound reflective) can be utilized, such as aluminum, hard plastic, sand, and metal particles. For example, the echogenic material can be any of those materials described in U.S. Pat. No. 5,201,314 and U.S. Pat. No. 6,106,473, or a combination of those materials. In another embodiment, the imageable material is a radio-opaque material (such as barium sulfate, tantalum, and/or gadolinium particles) that can be imaged with radiographic equipment (e.g., an x-ray machine or computed tomography (CT) scanner). In a further embodiment, the imageable material is a substance that can be imaged using magnetic resonance imaging/spectroscopy (MRI/MRS) equipment. Other imageable materials include those materials detectable through single photon emission tomography (SPECT) or positron emission tomography (PET), for example. The component or components of the thrombectomy device 10 can be wholly or partly composed of the imageable material. As indicated above, the imageable material can be in the form of a coating or film on an underlying substrate.

Contrast media, such as dyes, can also be used in conjunction with the appropriate imaging equipment in order to discern more details within the biological lumen. For example, barium-containing and iodine-containing dyes can be administered in conjunction with x-ray or CT imaging. Gadolinium, for example, can be used in conjunction with MRI imaging.

Optionally, the device 10 of the present invention can further include a means for providing a jet or jets of fluid under pressure to the distal end 26 of the rod 24, and/or at any point or points along the rod's length. For example, the rod 24 of the device 10 can be hollow and in operable communication with a pump that provides fluid under pressure to the distal end of the rod 24, where it exits the rod 24 through an outlet. The fluid jet can facilitate disruption of occlusions within the biological lumen.

Optionally, the device 10 of the present invention can include a means for vacuuming occluding debris from the lumen at the distal end 26 of the rod 24, and/or at any point or points along the rod's length. For example, the rod 24 of the device 10 can be hollow and in operable communication with a means for providing negative pressure to the interior of the rod, such that occlusive debris is drawn into inlets along the length and/or the end of the rod 24. Optionally, the device 10 can include both a jet means and a vacuum means, as described above. In one embodiment, the jet means and vacuum means can be alternatively operated to expel fluid from the device 10, in order to disrupt an occlusion, and to take up the occlusive debris upon activation of the vacuum means.

In addition to natural biological conduits of the body, such as blood vessels (veins, arteries, etc.), ureter, urethra, fallopian tube, bile duct, intestine, and the like, the device 10 and methods of the present invention can be utilized to remove occlusive materials from other biological or artificial conduits, such as arterial or venous catheters, stents, grafts, such as peripheral femoral-popliteal, coronary bypass grafts and dialysis access grafts, and fistulas.

The occlusion-removing device 10 of the present invention can be utilized to disrupt and/or remove occlusive material from natural or artificial lumens within humans or animals, such as non-human mammals. Thus, the device 10 of the present invention can be used in a variety of veterinary applications in order to treat domesticated or non-domesticated animals. The dimensions of the various components of the device 10 can be optimized for the particular animal subject.

Figures 7A, 7B:
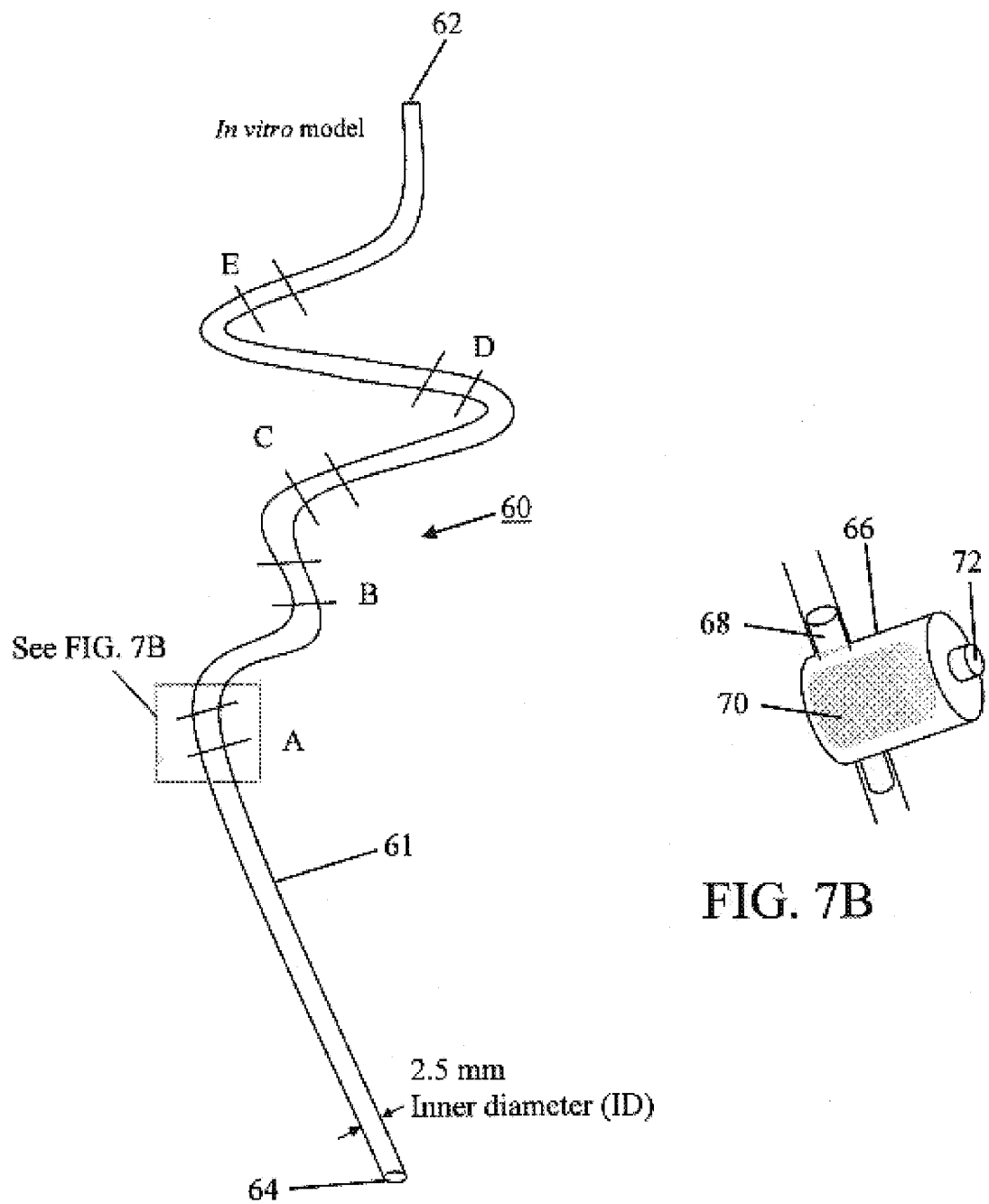
FIGS. 7A and 7B show an in vitro human middle carotid artery (MCA) model of the present invention, with A, B, C, D, and E representing different locations of the MCA.

In another aspect, the present invention concerns a device 60 useful as an in vitro model of luminal occlusion, such as that shown in FIGS. 7A and 7B, and methods for using the device 60 to test the efficacy of devices and methods for treating luminal occlusions. The device 60 includes a flexible hollow tube 61 having a first end 62 and second end 64. The flexible tube 61 can be composed of any material, such as silicone, which permits bending of the tube 61 into a tortuous shape, if desired. For example, the flexible tube can be composed of one or more melt-processible or non-melt-processible polymers; polyurethane; polyethylene; nylon; PEBAX; polyvinylchloride (PVC); thermoplastic elastomers; polyesters; and resin blends.

As shown in FIG. 7A, one or more bends can be placed in the tube 61 in order to simulate vasculature of the brain, for example. At one or more points along the length of the tube 61, occlusion sites can be established. In one embodiment, each occlusion site (A, B, C, D, E) has a three-way receptacle 66 (also referred to herein as a "clot holder") with ports 68 (also referred to herein as "fittings") connecting the receptacle 66 to the tube 61. The three-way receptacle 66 contains an occlusion 70, such as a naturally occurring or artificial clot. The receptacle 66 can further include an access port 73 for inserting an occlusion 70. The diameter and length of the tube 61 are preferably of dimensions to accommodate a particular test device to be inserted into the first or second ends 62, 64 of the tube 61 and to mimic the particular artificial or biological lumen to be modeled. Optionally, the tube 61 can have one or more branches and sub-branches. The tube 61 can contain a fluid, such as saline or blood, to mimic a biological vessel. The test device can be inserted into either end of the tube 61 and navigated to an occlusion site to act on an occlusion 70. The performance of the test device can then be evaluated. Test criteria will depend upon the nature of the technique and/or test device and the objective to be achieved.

The terms "comprising", "consisting of" and "consisting essentially of" are defined according to their standard meaning. The terms may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "an expandable balloon" includes more than one such balloon. A reference to "an elastic sheath" includes more than one such sheath. A reference to "a compartment" (i.e., "a cage") includes more than one such compartment. A reference to "an occlusion site" includes more than one such occlusion site, and the like.

All patents, patent applications, provisional applications, and publications referred to or cited herein, whether supra or infra, are incorporated herein by reference in their entirety to the extent they are not inconsistent with the explicit teachings of this specification.

Following are examples which illustrate procedures, including the best mode, for practicing the subject invention. These examples should not be construed as limiting. All percentages are by weight and all solvent mixture proportions are by volume unless otherwise noted.

EXAMPLE 1

Construction of a Thrombectomy Device

A thrombectomy device of the subject invention has been made in a modular fashion. The device consists of an elastomeric polymer tube of an appropriate size and a balloon catheter.

Tubes were made from CARBOSIL 40 90A (The Polymer Technology Group, Inc., Berkeley, Calif.), a solution grade elastomeric, tear-resistant silicone-polyurethane thermoplastic copolymer, by the dip-coating method. Several 21 (0.80 mm outer diameter, OD) gauge injection needles (MONOJECT from Sherwood Medical, St. Louis, Mo.) were used as mold substrates. Each needle was 1.5 inches long and the size (OD) of the needle represents approximately the inner diameter (ID) of the resulting tube. Two times dipping of each needle in 15 wt % polymer solution in tetrahydrofuran (THF) at about a 4 mm/sec withdrawal rate and a 30 minute interval between two successive dippings formed an approximately 90 µm thick polymer coating. Coated needles were then vacuum-dried. Coating on both ends of the needle was non-uniform. Therefore, keeping a uniform section of 30 mm long coating around the middle of the needle, the remaining coating was carefully cut by a sharp surgical razor blade (MILTEX Surgical Blades, model 4197 #11, MILTEX Instrument Company, Inc., Bethpage, N.Y.) and then removed. At this point, the coating could be detached in the form of a uniform tube.

Without detaching the coating from the needles, a pattern was made on the coating manually by a sharp black permanent marker, as shown in FIGS. 1A and 1B, (SHARPIE Ultra Fine Point Permanent Marker from SANFORD Corporation, Bellwood, Ill.). The pattern was along the length and around the needle. A total of 5 slits 20 were then cut along the pattern with a stainless steel surgical blade of about 10 µm tip size. Slits 20 were 10 mm long and the spacing between two slits 20 (defining a band 21 there between) was about 550 µm. This step was carried out under a microscope. Needles were then immersed in 60% acetone in water (V/V) for 5 minutes for swelling the polymer. The coating was then detached in the form of a uniform tube when pushed lightly off the needle. The actual modified polymer tube is shown in FIG. 11.

A SENTRY balloon catheter was purchased from BOSTON SCIENTIFIC-TARGET, Fremont, Calif. The balloon diameter and the balloon length were 3.5 mm and 10 mm when inflated. The balloon portion of the catheter was modified by constraining more of the proximal end of the balloon than the distal end, as shown in FIG. 2A, or by constraining about equal portions of the proximal end and distal end of the balloon, as shown in FIGS. 2B and 2C. The modified balloon portion was 2 mm long. This was done by wrapping around a stretchable, segmented polyurethane fiber (The Polymer Technology Group Inc., Berkeley, Calif.). Prior to wrapping, the fiber was pre-stretched to about 100% of its original length. When pressure was applied by injecting saline solution, only the unconstrained segment of the balloon 30 inflated, as shown in FIGS. 3A-3C.

The modified polymer tube was then swelled by immersion in 60% acetone in water (V/V) for 5 minutes. Swelling of approximately 40% of its original size occurred. The swelled tube was then slipped over the modified balloon in a desired location. The ID of the tube was smaller (about 0.2 mm) than the OD of the balloon. Once dried under the vacuum, the elastomeric tube captured the modified balloon firmly, as shown in FIGS. 4A-4C, with the actual device shown in FIG. 11.

Two preliminary tests were performed on the thrombectomy device: mechanical testing and in vitro performance testing.

EXAMPLE 2

Mechanical Testing of a Modified Balloon Under Applied Saline Pressure

Figure 6:
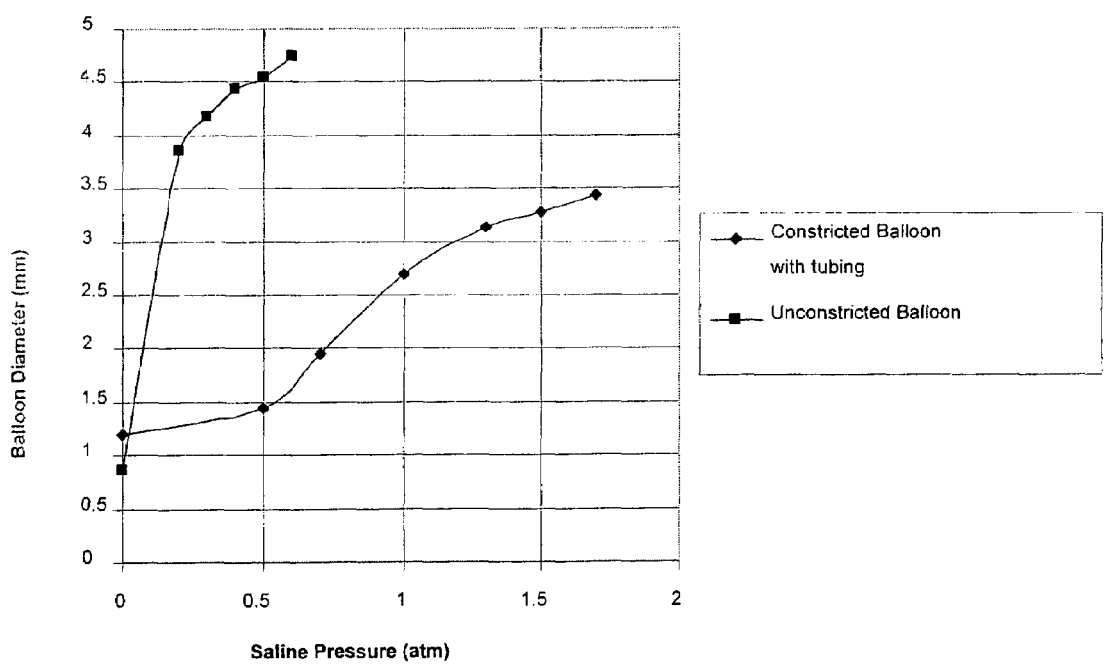
FIG. 6 shows a plot (calibration curve) of balloon diameter versus saline pressure. A control experiment with a bare balloon was performed and compared with the device. As expected, higher pressure was required to inflate the modified balloon in the device.

To determine the inflated balloon size with respect to the applied saline pressure, the device was installed on a micromanipulator. Using a digital inflation device and fluid dispensing syringe (MONARCH 25, MERIT MEDICAL SYSTEMS, Inc., South Jordan, Utah) the saline pressure was applied. The micromanipulator read the inflated balloon diameter quite accurately at different saline pressures. The digital inflation device showed the applied saline pressure directly. A plot (calibration curve) of balloon diameter versus saline pressure was constructed as shown in FIG. 6. A control experiment with a bare balloon was performed and compared with the device. As expected, higher pressure was required to inflate the modified balloon in the device. This type of calibration curve will be helpful for both in vitro and in vivo device operation.

EXAMPLE 3

In Vitro Performance Testing of the Thrombectomy Device in Silicone Tubing 40 cm long silicone tubing (ID 2.5 mm) was selected for the preliminary in vitro performance testing of the device 60. Two syringes were placed at both ends of the tube 61. Due to the flexible nature of the tube 61, an approximately tortuous shape could be given without kinking, as shown in FIG. 7A. Rabbit blood clots were used as models for the experiment. 1 ml of blood was allowed to coagulate in a 7 ml sterile blood collection tube for a period of 1 hour. The tube 61 was then opened and the bulk clot was removed and cut in half. Each section was weighed and recorded. The silicone tube 61 was prepared by flushing it with saline solution to remove any air bubbles from the tube 61. The blood clot was placed in a 3 ml syringe and injected into the silicone tube 61. Saline was then injected into the silicone tube 61 until the clot reached approximately 20 cm from the proximal end (first end, 62) of the tube 61. The syringe on the distal end (second end, 64) was kept attached to the silicone tube 61, but the proximal syringe was replaced with a 3-way device that allowed the catheter to be inserted.

The thrombectomy device 10 was first navigated through the tube 61 and passed through the emboli. The thrombectomy device 10 was then slowly deployed up to a desired size (about 2.2 mm) and pulled back. The cage structure was able to grab the emboli and move it out of the tube 61.

EXAMPLE 4

Materials for Making the Elastic Sheath

This component is the most important part of the thrombectomy device because it will directly contact and manipulate the thrombus. A modified balloon catheter will assist this component to make its cage-like shape when deployed.

Tear-resistant biocompatible elastomeric polymer materials will be chosen for making tubes. Two types of commercially available solution grade (SG) thermoplastic materials will be selected: a polyurethane (TECOFLEX SG-80A, THERMEDICS Polymer Products, Woburn, Mass.); and a few silicone-polyurethane copolymers (CARBOSIL 40 90A, PurSil 20 80A and PurSil AL5 75A, The Polymer Technology Group Inc., Berkeley, Calif.). TECOFLEX SG-80A is an aliphatic polyether-based thermoplastic polyurethane (TPU). PURSIL silicone-polyether-urethane and CARBOSIL silicone-polycarbonate-urethane are thermoplastic copolymers containing silicone in the soft segment. PURSIL 20 80A is an aromatic silicone polyetherurethane whereas PURSIL AL5 75A is an aliphatic silicone polyetherurethane. Table 1 lists some of the physical test data of these materials reported by the manufacturers. From the table it is clear that these materials cover a range of mechanical properties. The purpose of selecting all four materials under this study is to find the right material for the optimized device.

TABLE 1

Physical Test Data of Elastomeric Polymer Materials

| Elastomer | Tensile Stress at 100% Elongation (psi) | Tensile Stress at 300% Elongation (psi) | Ultimate Tensile Strength (psi) | Ultimate Elongation (%) | Tear Strength, die "C" (pli) |
|---|---|---|---|---|---|
| TECOFLEX EG-80A | 300 | 800 | 5800 | 660 | N/A |
| PURSIL 20 80A | 270 | 570 | 5300 | 900 | 390 |
| PURSIL AL5 75A | 900 | 1630 | 4900 | 770 | 115 |
| CARBOSIL 40 90A | 1310 | 2400 | 4300 | 530 | 500 |

The data for TECOFLEX EG-80A represent data for extrusion grade materials. The solution grade data are not available. The solution grades differ from the extrusion grades in that they contain no melt processing lubricants.

If required, in order to clearly visualize the tube under a fluoroscope while performing in vivo tests, the tube can be constructed so as to be radio-opaque. Radio-opaque grade TECOFLEX is available with 20 wt % and 40 wt % loading of barium sulfate. Other polymers could be either blended with barium sulfate or could be custom-blended from the manufacturer.

The dip-coating method will be used to make polymer tubes. TECOFLEX EG-80A is soluble in N, N-dimethylacetamide (DMAC), and other silicone-polyurethane copolymers are soluble in tetrahydrofuran (THF). Tubes will be made using 21 gauge needles (OD 0.8 mm). The inner diameter (ID) of the tube will be 0.8 mm or little less, if the polymer shrinks after drying. Tube thickness generally depends upon three parameters: the polymer concentration; the total number of dippings; and the withdrawal rate. By proper adjustment of these three parameters, tubes will be made of about 100 μm in thickness. Table 2 shows the details.

TABLE 2

Elastic Sheath Design

| Needle size (gauge) | Number of slits | Pattern | Slit length (mm) (approximately) | Tube thickness (μm) (approximately) | Calculated spacing between two adjacent slits (μm) (approximately) |
|---|---|---|---|---|---|
| 21 (0.8 mm OD) | 5 | A | 10 (type 1A) and 15 (type 2A) | 100 | 630 |
|  |  | B | 6.5 (type B) |  |  |

Tubes will be modified in three different patterns (A, B, and C), as shown in FIGS. 2A-2C, respectively, to produce elastic sheaths 40 of the subject invention. Patterns A and B will produce sheaths 40 with 10 mm and 15 mm long slits 20, respectively. In structure A, the modified balloon 30 will be located at one end of the slits 20 (towards the catheter tip); whereas, in structure B, the balloon 30 will be located in the middle along the length of the slits 20. The operation of the device with structure A is "one way" such that, after being passed through the thrombus, the cage structure is deployed and then pulled back through the thrombus, disrupting the thrombus and capturing thrombotic debris. Unlike structure A, structures B and C have double cage structures, which means that they function to disrupt and capture thrombus both when pushed and pulled through the occluded region of the vessel. Therefore, it is expected that the double cage structure will have an advantage in grabbing more thrombus, compared to the single cage structure. As described previously, longitudinal slits 20 will be made under a microscope using sharp surgical blade of about 10 micron tip size. The total number of longitudinal slits 20 in each elastic sheath 40 will be 5.

EXAMPLE 5

Mechanical Testing of an Elastic Sheath

All mechanical testing will be performed using an INSTRON model 4301 (INSTRON Corporation, Canton, Mass.). Using an appropriate load cell (e.g., tension/compression 250 gm load cell, INSTRON model: type 00), a complete stress-strain profile for both modified and unmodified tubing will be generated. By this measurement, the mechanical characteristics of all three structures, A, B and C, will be compared directly.

Flexibility and maneuverability testing are useful to predict the feasibility of navigating the device through the tortuous intracranial vasculature system in the brain. A three-point bend test will be conducted. A bend test fixture and an "S" hook for the bend test will be designed and constructed. Thin tubes will likely kink while performing the bend test. In order to overcome this problem, compliant (highly flexible) silicone rods of an appropriate size will be made and used as substrate for the tube. Once the tube is mounted over the rod, it will not kink while performing the bend test. Approximately 0.8 mm OD silicone rods will be made from two-component platinum cure SILASTIC T2 (DOW CORNING, Midland, Mich.) mold making rubber. Appropriately sized (e.g., about 0.8 mm ID) melting point glass capillary tubes (KIMAX-51 borosilicate glass from KIMBLE-KONTES, Vineland, N.J.) will be used as a mold substrate. Once cured inside the capillary tube, the silicone rods will be removed from the mold by dissolving the glass in hydrofluoric acid.

The measurement of the string tear strength will be important in order to prevent breaking of the strings in the cage structure during the thrombus retrieval process. We will first mount the modified tube on an appropriate rigid rod (stainless steel needle), and then both ends of the tube will be fixed to the rod by tying with non-stretchable fiber. Using an INSTRON setup, each string will be pulled with respect to the rest until it breaks. A stress versus displacement plot will be generated for the comparison of string strengths of three different structures.

EXAMPLE 6

In Vitro Performance Testing of the Thrombectomy Device in a Middle Carotid Artery (MCA) Model SENTRY balloon catheters (150 cm long) will be purchased from BOSTON SCIENTIFIC-TARGET, Fremont, Calif. The balloon diameter and the balloon length are 3.5 mm and 15 mm, respectively, when inflated. The diameter of the catheter at the balloon is 0.86 mm when un-inflated. The balloon portion of the catheter will be modified to create balloon types A and B by constraining it at both ends into a 2 mm long balloon in the middle, as shown in FIGS. 2A and 2B. Balloon type C (FIG. 2C) will be made similarly as type A and B with the exception that, in type C, the balloon will be further split into two halves by constraining the middle portion of the balloon. This will be done by wrapping around stretchable, segmented polyurethane fiber. Prior to wrapping, the fiber will be pre-stretched about 100% of its original length. The balloon modification steps will be carried out under a microscope. When pressure is applied by injecting saline, only the unobstructed balloon portion will inflate, as shown in FIGS. 3A-3C. Mechanical testing of the modified balloon catheter will involve measurement of the balloon diameter increase with respect to the saline pressure to determine the optimum inflation pressure. Mechanical testing on these modified balloons will then be performed. A plot will be constructed showing the increase of the balloon diameter with respect to the increase of the saline pressure. This plot will facilitate the determination of optimum saline pressures for a desired balloon size.

Both the modified balloon catheter and the modified tube will be re-inspected under a microscope before the final assembling. The modified polymer tube will then be swelled by immersing it in an appropriate solvent as described before. Swelling of approximately 30% of its original size would be sufficient to slip it over the modified balloon. The ID of the tube will purposely be made smaller than the OD of the balloon portion of the catheter. Once dried under the vacuum, the elastomeric tubing will capture the modified balloon firmly. Schematic representation of the device is shown in FIGS. 4A-4C. In order to secure the thrombus inside the cage structure, a "spider-web" like pattern can be made near the balloon of the device, covering about 50% of the tube length, for example, as shown in FIG. 5. Polymer solution (same as the tube material) will be directly applied in the form of a fine fiber onto the inflated device in such a way that it will connect the elastomeric strings.

The mechanical testing will be performed using an Instron setup as described earlier in the preliminary study section. The flexibility testing of the device will be performed by a three point bend test. A calibration curve will be generated showing maximum cage diameter with respect to the saline pressure. This experiment will help for in vitro and in vivo testing of the device.

A polypropylene tube (PP) of 2.50 mm ID will be used for making the model of the tortuous MCA. This type of tube may kink while bending it to give the tortuous shape. To overcome this problem, an appropriate size copper wire will be inserted inside the PP tube first to give the right shape to the tube. Translucent silicone glue (SILASTIC T2 from DOW CORNING) will be applied over the PP tube and then it will be heat treated. Once cured, silicone oil will be injected into the tube to make the tube interior slippery. Then the structure will be straightened and the copper wire support will be removed. Once released, the tube will return to its tortuous shape. Silicone over-coating should reinforce and retain the structure. It will then be cleaned and installed as shown in FIG. 7A.

Clots will be made directly from rabbit blood. The plastic MCA model will be marked A, B, C, D and E, as shown in FIG. 7A, which will represent different locations of the MCA. The tube will then be cut at each location to attach a clot holder. The clot holder will be a detachable silicone pouch with two openings, as shown in FIG. 7B. Both openings of the holder will be attached to the model through plastic fittings. This pouch will then be filled with condensed clot (the clot condensation will be done by centrifugation). Before operation of the device, the model will be bathed with saline solution. All locations, from A through E, will be tested with the device to evaluate the device performance at each location.

The feedback from the in vitro testing will help for the further development of the device. A repeated redesigning and remanufacturing process will be carried out to optimize the device performance for three different cage patterns (A, B and C). This investigation will provide information on the best polymer material (out of four different materials) for each cage pattern.

EXAMPLE 7

In Vivo Performance Testing of the Thrombectomy Device in a Rabbit Kidney Occlusion Model A rabbit kidney occlusion model closely mimics the MCA in humans (in terms of the lumen size) will be utilized. Prior to the surgical procedure, the animal will be sedated with acetylpromazine (0.5-2.0 mg/kg SQ or IM) and 0.5 ml of blood will be drawn from the central auricular artery and allowed to coagulate in a 3 ml blood collection tube with a wire for one hour at 37° C. This autologous thrombus will be used for creation of the thromboembolic occlusion. The animal will then be weighed to determine proper injectable anesthetic doses, and placed under general anesthesia. General anesthesia will be induced with KAX (0.6 ml/kg), a mixture of 10 ml ketamine HCl (PHOENIX PHARMACEUTICALS, 100 mg/kg), 2 ml acepromazine maleate (PHOENIX PHARMACEUTICALS, 10 mg, kg), and 1.5 ml xylazine (PHOENIX PHARMACEUTICALS, 100 mg/kg).

Figure 8:
FIG. 8 shows angiography of a right kidney and renal artery of a rabbit.

Following sufficient sedation, the animal will be intubated and attached to a ventilator providing an oxygen mixture (21% oxygen USP, 79% nitrogen). The surgical site will then be shaved, prepped and draped in a sterile fashion using 3 cycles of surgical scrub and alcohol/chlorhexidine rinse. The level of anesthesia will be monitored by heart rate, respiration rate, temperature, animal movement, pupillary size, toe pinch reflex, blinking reflex, fluid balance tearing, and salivation. Additional doses of KAX (0.3 ml/kg) will be given to maintain general anesthesia. An incision will be made in the hindlimb of the rabbit to expose the femoral artery for catheterization. A slit will be cut in the artery with micro-scissors and a 4F introducer sheath will be placed into the femoral artery and secured in place with a 4.0 silk suture. A 3F angiographic catheter and a guidewire will then be advanced with fluoroscopic guidance towards the right kidney until catheterization of the renal artery is achieved (1.5-3.5 mm diameter). Digital subtraction angiography will be performed to confirm proper placement of the catheter (FIG. 8).

Figure 9:
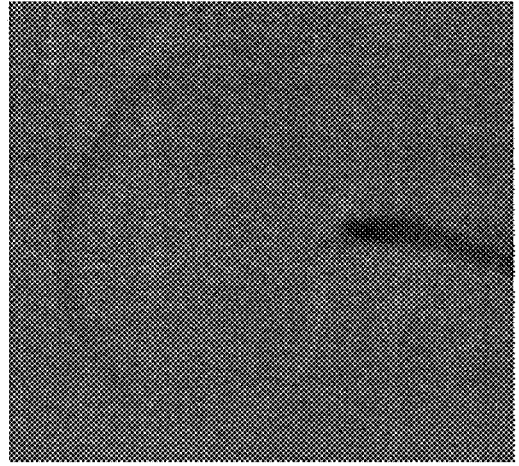
FIG. 9 shows angiography of the kidney shown in FIG. 8, with successful thromboembolism evident.

After the previously obtained autologous thrombus has matured for 1 hour, it will be cut into 2 sections and a section will be placed into a 0.9% saline filled syringe for embolization. The thrombus segment and saline will then be injected into the lower branch of the right renal artery. Without moving the catheter, the second clot segment will be injected. Successful thromboembolism of the renal artery will be confirmed with angiography (FIG. 9). The left renal artery will then be catheterized with the same technique. The same procedure as described above will be repeated in the left renal artery. All of the animals will remain under general anesthesia for 30 minutes after thrombus injection, but before initiating any treatment.

Figure 10:
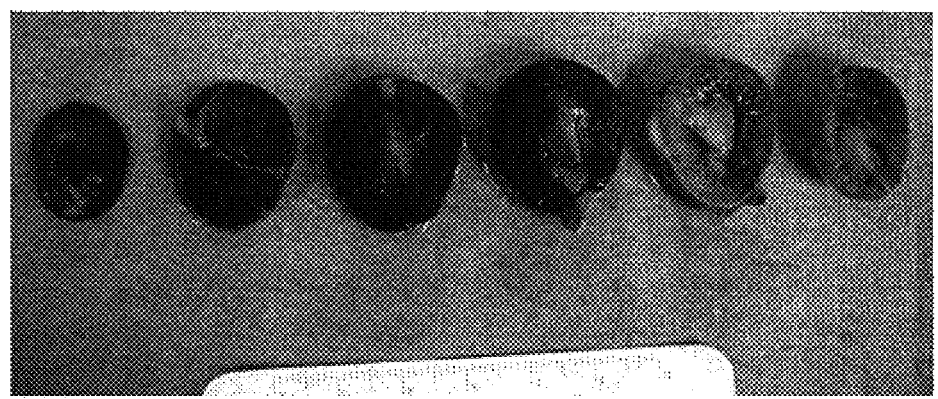
FIG. 10 shows photographs of sliced 5 mm sections of kidney.

Final angiography will be performed bilaterally 4 hours after clot injection to determine recanalization status and will be graded with the TIMI (Thrombosis in Myocardial Infarction) score, which is a commonly used system for grading recanalization. The animal will be euthanized with an overdose of sodium pentobarbital. The kidneys will be surgically removed, sliced into 5 mm sections and allowed to soak in TTC stain for 30 minutes. The specimens will then be digitally photographed (FIG. 10) and the infarction percent of each kidney will be calculated.

It should be understood that the example and embodiments described herein are for illustrative purposes only and that various modifications or changes in light thereof will be suggested to persons skilled in the art and are to be included within the spirit and purview of the application.

We claim:

1. A method for removal of thrombus material from an intracranial blood vessel of a human subject, using a device having a balloon-activated compartment, said method comprising:
    (a) inserting the device into the intracranial blood vessel of the subject, wherein the device comprises a rod, an elastomeric sheath that ensheaths at least a segment of the rod, and an expandable balloon for expanding the elastomeric sheath, wherein the expandable balloon, upon initiation of expansion, provides radial pressure to a portion of the elastomeric sheath, causing an adjacent segment of the elastomeric sheath to be displaced outwardly away from the rod segment, thereby forming the compartment beneath the displaced elastomeric sheath segment, wherein the displaced elastomeric sheath segment comprises a plurality of slits that expand upon expansion of the balloon, and wherein the compartment has a volume that is larger than the space occupied by the expanded balloon;
    (b) expanding the balloon;
    (c) capturing the thrombus material within the compartment, wherein said capturing of the thrombus material includes:
        moving the device within the blood vessel;
        bringing the displaced elastomeric sheath segment into contact with the thrombus material; and
        causing the thrombus material to pass through a slit of the displaced elastomeric sheath segment;
    (d) at least partially collapsing the balloon, thereby collapsing the compartment; and
    (e) withdrawing the device from the blood vessel.

2. The method of claim 1, wherein the intracranial blood vessel is an intracranial artery.

3. The method of claim 1, wherein at least one portion of the device is impregnated or coated with a biologically active agent.

4. The method of claim 1, wherein the plurality of slits are longitudinally arranged on the displaced elastomeric sheath segment, and wherein each slit is separated from adjacent slits by a longitudinal band of elastomeric material.

5. The method of claim 4, wherein the longitudinal bands are cross-linked with a plurality of lateral bands that bridge the longitudinal slits, thereby forming a mesh.

6. The method of claim 4, wherein the longitudinal bands make shearing contact with the thrombus material.

7. The method of claim 1, wherein the expandable balloon comprises at least one radially constrained portion and at least one radially unconstrained portion.

8. The method of claim 7, wherein when pressure is applied to the interior of the expandable balloon, the at least one radially unconstrained portion expands to form at least one sphere or spheroid shape.

9. The method of claim 8, wherein the at least one radially constrained portion is constrained with a fiber that is wrapped around the at least one radially constrained portion.

10. The method of claim 8, wherein the compartment is substantially conical in shape.

11. The method of claim 1, wherein the elastomeric sheath comprises a flexible polymer tube.

12. The method of claim 1, wherein the elastomeric sheath comprises a thermoplastic elastomer.

13. The method of claim 1, wherein the elastomeric sheath comprises a flexible polymer selected from the group consisting of silicone, polyurethane, silicone-polyurethane copolymer, and styrene-ethylene-butylene-styrene (copolymer).

14. The method of claim 1, wherein the device is at least partially composed of an imageable material.

15. The method of claim 1, wherein the portion of the elastomeric sheath receiving radial pressure from the balloon has a length that is shorter than the length of the adjacent segment of the elastomeric sheath that is displaced upon expansion of the balloon.

16. The method of claim 1, wherein the volume of the compartment increases with the diameter of the elastomeric sheath segment upon expansion of the balloon.

17. The method of claim 1, wherein the compartment is proximal to the balloon.

18. The method of claim 1, wherein the compartment is distal to the balloon.

19. The method of claim 1, wherein the rod has a distal end and a proximal end, and wherein the compartment has a diameter that decreases toward the proximal end or distal end of the rod.

20. The method of claim 1, wherein the compartment circumferentially surrounds the rod segment.

21. The method of claim 1, wherein the expandable balloon comprises two or more expandable balloons.

22. The method of claim 1, wherein when the balloon is collapsed, the plurality of slits are closed.

23. The method of claim 1, wherein the balloon comprises at least one radially constrained portion and at least one radially unconstrained portion, and wherein the rod segment is ensheathed by the at least one radially constrained portion of the balloon.

24. The method of claim 1, wherein the expandable balloon comprises a single expandable balloon.

25. The method of claim 1, wherein said moving the device within the conduit comprises moving the device in a back-and-forth and/or twisting motion within the blood vessel.

26. The method, according to claim 1, wherein said capturing of the thrombus material consists of:
   moving the device within the blood vessel;
   bringing the displaced elastomeric sheath segment into contact with the thrombus material; and
   causing the thrombus material to pass through a slit of the displaced elastomeric sheath segment.

27. The method, according to claim 1, wherein said capturing of the thrombus material consists essentially of:
   moving the device within the blood vessel;
   bringing the displaced elastomeric sheath segment into contact with the thrombus material; and
   causing the thrombus material to pass through a slit of the displaced elastomeric sheath segment.

28. The method of claim 1, wherein the thrombus material has caused an ischemic thromboembolic stroke in the subject.

* * * * *

UNITED STATES PATENT AND TRADEMARK OFFICE
CERTIFICATE OF CORRECTION

PATENT NO. : 7,618,434 B2  
APPLICATION NO. : 10/844737  
DATED : November 17, 2009  
INVENTOR(S) : Swadeshmukul Santra et al.

It is certified that error appears in the above-identified patent and that said Letters Patent is hereby corrected as shown below:

Column 22,  
Line 4, "the example and embodiments" should read --the examples and embodiments--.

Column 22,  
Line 8, "of the application." should read --of this application.--.

Signed and Sealed this

Fifth Day of January, 2010

David J. Kappos  
*Director of the United States Patent and Trademark Office*